United States Patent [19]

Yabe et al.

[11] Patent Number: 5,460,167
[45] Date of Patent: Oct. 24, 1995

[54] ENDOSCOPE COVER WITH CHANNEL

[75] Inventors: Hisao Yabe; Hideo Itoh, both of Hachioji; Yoshio Tashiro, Hino; Yoshihiro Iida, Tama; Akira Suzuki, Hachioji; Minoru Yamazaki, Hachioji; Osamu Tamada, Hachioji; Tatsuya Furukawa, Hachioji, all of Japan

[73] Assignee: Olympus Optical Co., Ltd., Tokyo, Japan

[21] Appl. No.: 38,650

[22] Filed: Mar. 29, 1993

[30] Foreign Application Priority Data

| Mar. 4, 1993 | [JP] | Japan | 5-08833 U |
| Mar. 4, 1993 | [JP] | Japan | 5-08834 U |
| Mar. 4, 1993 | [JP] | Japan | 5-044134 |

[51] Int. Cl.⁶ ............................................. A61B 1/00
[52] U.S. Cl. ............................................. 600/107; 600/123
[58] Field of Search ................................................ 128/4, 6

[56] References Cited

U.S. PATENT DOCUMENTS

| Re. 34,110 | 9/1992 | Opie . | |
| 3,162,190 | 12/1964 | Del Gizzo . | |
| 3,608,555 | 9/1971 | Greyson | 128/348 |
| 3,924,608 | 12/1975 | Mitsui | 128/4 |
| 4,245,624 | 1/1981 | Komiya | 128/4 |
| 4,347,204 | 8/1982 | Takagi et al. | 264/127 |
| 4,452,236 | 6/1984 | Utsugi | 128/4 |
| 4,593,680 | 6/1980 | Kubokawa | 128/4 |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,841,949 | 6/1989 | Shimizu et al. | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,945,894 | 8/1990 | Kawashima | 128/6 |
| 4,991,564 | 2/1991 | Takahashi | 128/4 |
| 4,991,565 | 2/1991 | Takahashi et al. | 128/4 |
| 4,997,084 | 3/1991 | Opie | 206/364 |
| 5,025,778 | 6/1991 | Silverstein et al. | 128/4 |
| 5,050,585 | 9/1991 | Takahashi | 128/4 |
| 5,058,567 | 10/1991 | Takahashi | 128/4 |
| 5,305,736 | 4/1994 | Ito | 128/6 |

FOREIGN PATENT DOCUMENTS

| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |

(List continued on next page.)

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

An endoscope cover with a channel covers at least an inserted portion of an endoscope. The endoscope cover has a treatment tool channel into which a treatment tool is inserted and incorporates a treatment tool raising device for moving, to a predetermined position, the treatment tool inserted into the treatment tool channel and protruding from a distal end portion of the treatment tool channel. The endoscope cover includes an endoscope operating portion fixing port portion provided at a proximal end portion of an inserted portion covering portion which covers the inserted portion of the endoscope. The port portion fixes an operating portion of the endoscope inserted into the inserted portion covering portion. A treatment tool raising device operating member connected to the treatment tool raising device for operating the treatment tool raising device is disposed in the endoscope operating portion fixing port portion.

2 Claims, 21 Drawing Sheets

FOREIGN PATENT DOCUMENTS

| | | |
|---|---|---|
| 1-140902 | 9/1989 | Japan . |
| 2-57228 | 2/1990 | Japan . |
| 2-54734 | 11/1990 | Japan . |
| 3-29634 | 2/1991 | Japan . |
| 3-29635 | 2/1991 | Japan . |
| 3-37029 | 2/1991 | Japan . |
| 3-13105 | 2/1991 | Japan . |
| 3-37030 | 2/1991 | Japan . |
| 3-221024 | 9/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| 3-101901 | 10/1991 | Japan . |
| 3-101902 | 10/1991 | Japan . |
| 4-325138 | 11/1992 | Japan . |

ENDOSCOPE COVER WITH CHANNEL

BACKGROUND OF THE INVENTION

1. Field of the Invention

The present invention relates to an endoscope cover with a channel which has at least a single channel, including a treatment tool channel through which a treatment tool, such as a clamp, is inserted, and which covers the inserted portion of an endoscope.

2. Description of the Related Art

In recent years, endoscopes have been extensively used in many fields including medicine. Endoscopes used in the medical field have a deficiency when inserted into an organism, in that the observation window provided at the distal end portion of an inserted portion may be covered with body fluid, preventing thorough observation. Hence, in order to make a fluid, such as a washing liquid or washing gas, flow by an operation conducted by the operator at the proximal end of the endoscope to remove the body fluid attached to the observation window, the endoscope may be provided with a gas or a liquid conduit. Endoscopes provided with a suction conduit through which unnecessary body fluid is sucked and drained are also known. Also proposed have been endoscopes provided with a treatment tool channel through which a tissue is collected using biopsy forceps, or through which a medical treatment is conducted using a treatment tool.

For endoscopy, a clean endoscope must be used which has been subjected to thorough washing and disinfection before inspection.

Therefore, in the endoscope provided with a conduit, such as a gas conduit, or a treatment tool channel, washing or sterilization is conducted on the endoscope which has been used on a patient. However, it takes time for washing or sterilization to be conducted completely, reducing the efficiency of the endoscope.

Hence, an endoscope covered type endoscope apparatus which eliminates washing or sterilization has been proposed. The endoscope itself is used while it is covered with an endoscope cover provided with a gas or liquid conduit or the like. After use, the endoscope cover alone is discarded and replaced with a new one. In this way, the endoscope itself remains clean even after use, and washing or sterilization of the endoscope itself is thus unnecessary.

Such an endoscope covered type endoscope apparatus has been disclosed in, for example, U.S. Pat. Nos. 4,646,722 and 3,162,190. In these endoscope apparatuses, an endoscope inserted portion is inserted into a cover so that it can be covered by the cover and thereby insulated from an external environment.

In the endoscope covered type endoscope apparatus of the above-described type, the inserted portion is washed or sterilized beforehand. The endoscope is inserted into the body cavity of a patient with the inserted portion of the endoscope covered with an endoscope cover for inspection or treatment. After use, the endoscope cover is removed and abandoned. Thus, since the endoscope cover is thrown away for each patient, washing or disinfection of the endoscope is unnecessary, and the endoscope is kept clean in a simple manner. The endoscope can be continuously used without being washed or disinfected again.

However, the endoscope covered type endoscope apparatus of the above-described type mainly employs a forward direct viewing type endoscope. An endoscope covered type endoscope apparatus employing a side-viewing type endoscope has not been proposed.

In the side-viewing type endoscope, the observation and illumination windows are provided at the distal end portion of the inserted portion in such a manner that they are directed sideways. Therefore, in a side-viewing type endoscope applied to the endoscope covered type endoscope apparatus, an endoscope cover having a different structure from one in the direct-viewing endoscope is used. Particularly, an endoscope cover with a channel, in which a channel, such as a fluid conduit, a suction conduit or a treatment tool channel, is provided, is different in the structure of the channels and that of the observation and illumination windows.

For example, in a side-viewing endoscope provided with a treatment tool channel, a treatment tool raising device for raising the distal end portion of a treatment tool, e.g., forceps, is provided. Since the treatment tool raising device has a complicated mechanism, it is not easy to provide the treatment tool raising device in an endoscope cover.

In an endoscope covered type endoscope with a treatment tool raising device in which a treatment tool raising lever for operating the treatment tool raising device is provided in the operating portion of the endoscope, as in the case of a standard endoscope which is repeatedly sterilized for use, mounting the cover on the endoscope for cover requires a complicated connecting operation, such as connection of a treatment tool raising wire for connecting, to the operating portion, the treatment tool raising lever to a treatment tool table.

SUMMARY OF THE INVENTION

An object of the present invention is to provide an an endoscope cover with a channel which enables the operability for mounting the endoscope cover to be improved in an endoscope covered type endoscope apparatus which incorporates a treatment tool raising device for raising a treatment tool or the like inserted into the channel.

Another object of the present invention is to provide an endoscope cover with a channel which has a simple and inexpensive treatment tool raising device.

Still another object of the present invention is to provide an endoscope cover with a channel which enables the operability of various operations to be improved in an endoscope covered type endoscope apparatus in which a covered endoscope is covered by the endoscope cover with the channel.

The present invention provides an endoscope cover with a channel which covers at least an inserted portion of an endoscope, which has a treatment tool channel into which a treatment tool is inserted and which incorporates a treatment tool raising device for moving, to a predetermined position, the treatment tool inserted into the treatment tool channel and protruding from a distal end portion of the treatment tool channel.

The endoscope cover includes an endoscope operating portion fixing port portion which is provided at a proximal end portion of an inserted portion covering portion for covering the inserted portion of the endoscope to fix an operating portion of the endoscope inserted into the inserted portion covering portion. A treatment tool raising device operating member connected to the treatment tool raising device for operating the treatment tool raising device is disposed in the endoscope operating portion fixing port portion.

Other features and advantages of the invention will be apparent from the following description taken in connection with the accompanying drawings.

DETAILED DESCRIPTION OF THE PREFERRED EMBODIMENTS

A first embodiment of the present invention will be described below with reference to FIGS. 1 through 7.

Figure 1:
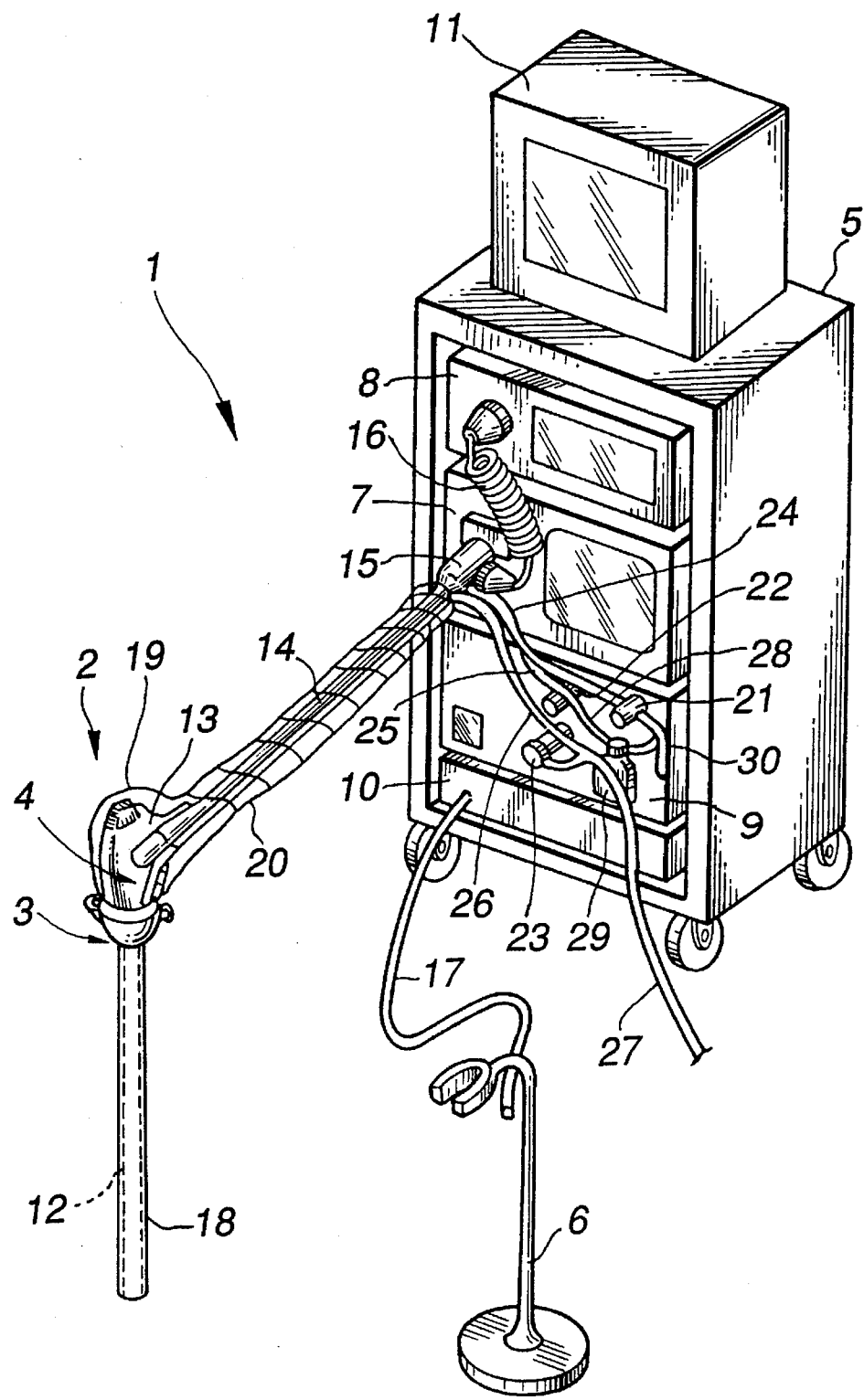
FIG. 1 illustrates the entire structure of an endoscope covered type endoscope apparatus.

As shown in FIG. 1, an endoscope covered type endoscope apparatus 1 includes an endoscope covered type endoscope (hereinafter referred to as a covered type endoscope) 2. The covered type endoscope 2 includes an endoscope cover with a channel in which a channel, such as a fluid conduit, a suction conduit or a treatment tool channel, is provided therein (hereinafter referred to as an endoscope cover) 3, and an endoscope to be covered by an endoscope cover (hereinafter referred to as a covered endoscope) 4 which is mounted in the endoscope cover 3. For endoscopy, the inserted portion or the like of the covered endoscope 4 is covered with the clean endoscope cover 3. After endoscopy is completed, the endoscope cover 3 is thrown away, while the covered endoscope 4 is covered by another clean endoscope cover 3 for reuse. Therefore, washing and sterilization of the endoscope, which would otherwise be conducted after endoscopy is ended, are unnecessary.

In addition to the covered type endoscope 2, the endoscope apparatus 1 further includes a cart 5 which is connected to the covered type endoscope 2 and incorporates various peripheral units therein, and a cover retaining tool 6 for retaining the covered type endoscope 2.

In the cart 5 are housed, for example, a light source unit 7, a video processor 8, a fluid control unit 9, an endoscope cover expander (hereinafter referred to as an expander) 10 used to mount the covered endoscope 4 in the endoscope cover 3. On the cart 5, a monitor 11 for displaying an endoscope image in response to a video signal received from the video processor 8 is placed.

In the covered endoscope 4, a large-diameter operating portion 13, also serving as a handle portion, is connected to the proximal end of a small-diameter endoscope inserted portion 12. A universal cord 14 extends from the side of the operating portion 13. A connector 15 is provided at an end portion of the universal cord 14.

The light source unit 7 is connected to the covered endoscope 4 with the connector 15 therebetween in such a manner that it can be removed from and mounted on the covered endoscope 4 to supply illumination light to the endoscope. The video processor 8 is connected to the covered endoscope 4 through a signal cable 16 extending from the side of the connector 15 in such a manner that it can be mounted on and removed from the covered endoscope 4 to drive an imaging means incorporated in the covered endoscope and to process a signal output from the imaging means. A standard video signal obtained by the video processor 8 is output to the monitor 11.

The expander 10 is connected to an expansion tube 17. The expander 10 blows an air into the endoscope cover 3 to inflate it. An inflated endoscope cover 3 can be readily mounted on or removed from the covered endoscope 4. The endoscope cover 3 is mounted on or removed from the covered endoscope 4 using the cover retaining tool 6. For example, the covered endoscope 4 is inserted into or removed from the endoscope cover 3 whose proximal end side is retained by the cover retaining tool 6.

The endoscope cover 3 includes a soft inserted portion covering portion 18, a thin and soft operating portion covering portion 19 made of a polymer, such as a vinyl chloride, and a universal cord covering portion 20, which respectively cover the inserted portion 12, the operating portion 13 and the universal cord 14 of the covered endoscope 4.

The fluid control unit 9 has a gas control valve 21, a liquid control valve 22, and a suction control valve 23, which are electromagnetic valves used to control gas and liquid supply and suction, respectively. The gas control valve 21, the liquid control valve 22 and the suction control valve 23 are respectively connected to a gas conduit 24, a liquid conduit 25 and a suction conduit 26 which extend from the inserted portion covering portion 18.

The suction control valve 23 is also connected to a suction tube 27 whose end portion is connected to a sucker (not shown) to suck an unnecessary body fluid or the like from the distal end portion of the endoscope. The liquid control valve 22 is also connected to a liquid tube 28 whose distal end portion is connected to a liquid tank 29. In addition, two gas tubes 30 extending from the fluid control unit 9 are connected to the gas control valve 21 and the liquid tank 29.

Figure 2:
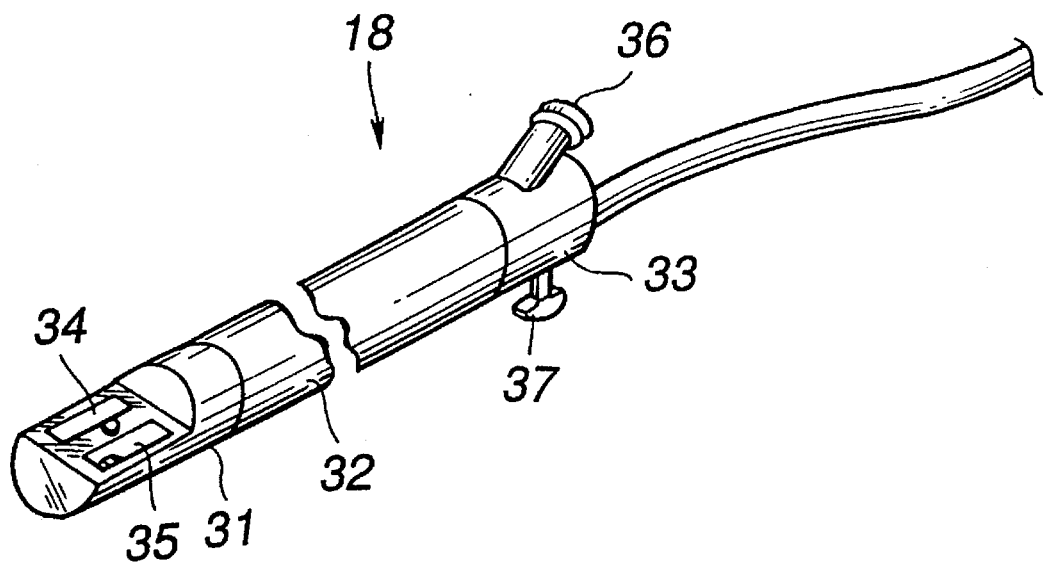
FIG. 2 is a perspective view illustrating a first embodiment of an endoscope cover according to the present invention.

FIG. 2 schematically illustrates the inserted portion covering portion 18 of the endoscope cover 3.

The inserted portion covering portion 18 includes a cover distal end constituting portion 31, an outer skin 32 and an endoscope operating portion fixing port portion (hereinafter referred to as a port portion ) 33 for fixedly connecting the operating portion 13 of the endoscope, which are disposed in that order with the cover distal end constituting portion 31 positioned closest to the distal end of the endoscope and which are hermetically connected to each other. The cover distal end constituting portion 31 has an open portion 34 for observation and an open portion 35 for a channel. A transparent cover glass is disposed on the open portion 34 for observation. The observation and illumination windows of the endoscope inserted into the cover oppose the open portion 34 for observation so that the operator can irradiate the portion to be inspected with illumination light and observe that portion to be inspected.

On the port portion 33 are provided a treatment tool insertion portion 36 which communicates with a treatment tool channel provided therein and a treatment tool raising lever 37 serving as a treatment tool raising device activating member for operating the treatment tool raising device which raises the distal end portion of a treatment tool, such as a clamp, inserted into the treatment tool channel from the treatment tool insertion port 36.

Figure 3:
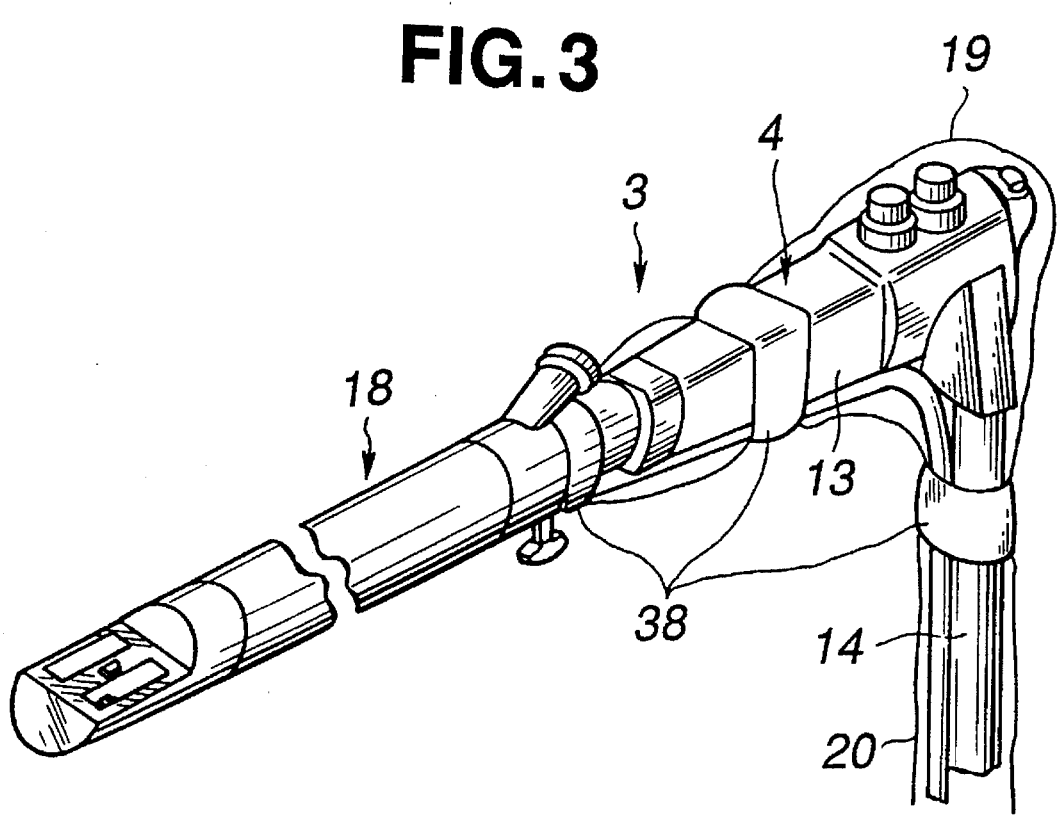
FIG. 3 is a perspective view showing how the endoscope cover of FIG. 2 is mounted on a covered type endoscope.

FIG. 3 illustrates how the endoscope cover 3 is mounted on the covered endoscope 4.

After the inserted portion 12 of the covered endoscope 4 is inserted into the inserted portion covering portion 18, the operating portion 13 of the endoscope is covered by the operating portion covering portion 19, and the universal cord 14 is covered by the universal cord covering portion 20, a fixing tape 38 is wound around the connected portions between the individual covering portions, whereby the individual portions of the covered endoscope 4 are hermetically covered and separated from the external environment by the endoscope cover 3 (including the inserted portion covering portion 18, the operating portion covering portion 19, and the universal cord covering portion 20).

Figure 4:
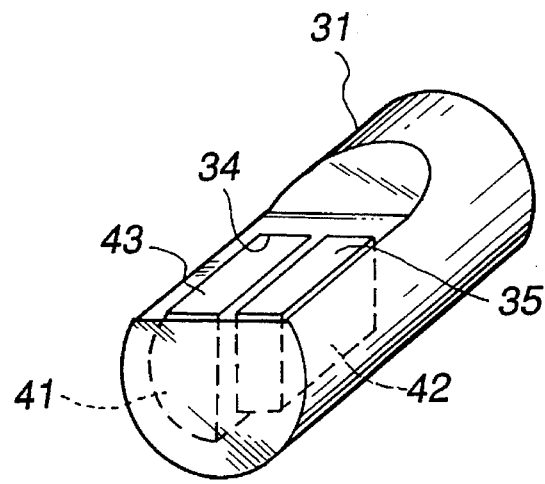
FIG. 4 is a perspective view of a distal end portion of the endoscope cover of FIG. 2.

FIG. 4 shows the structure of the cover distal end constituting portion 31 of the endoscope cover.

The cover distal end constituting portion 31 is preferably made of a hard resin, and has an endoscope distal end portion inserted hole 41 which communicates with the endoscope insertion channel provided in the inserted portion covering portion 18 and engages with the endoscope distal end portion, and a channel distal end portion 42 which communicates with the treatment tool channel. The distal end portion of the treatment tool channel is open through the channel open portion 35. A cover glass 43 is provided in the open portion 34 for observation disposed on the side of the endoscope distal end portion insertion hole 41. The cover glass 43 transmits light therethrough and separates the endoscope distal end portion provided in the insertion hole from the external environment.

Figure 5:
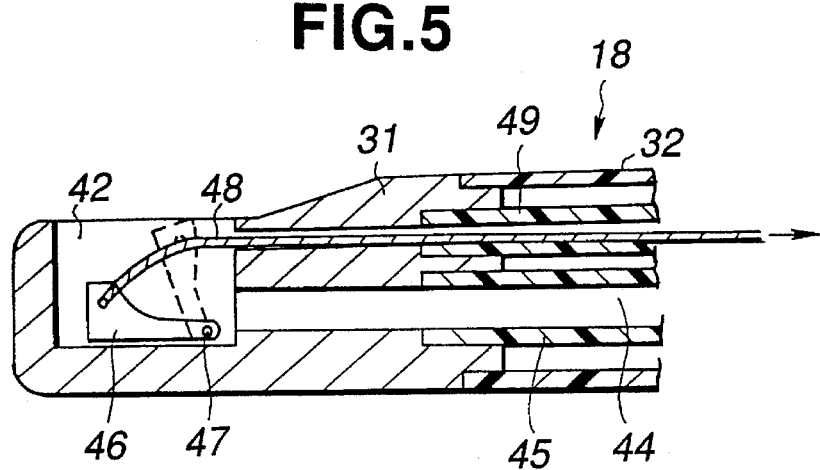
FIG. 5 is a cross-sectional view of the distal end portion of the endoscope cover of FIG. 2.

FIG. 5 is a longitudinal cross-sectional view of the distal end portion of the inserted portion covering portion 18 of the endoscope cover which includes the cover distal end constituting portion 31.

A channel tube 45 constituting a treatment tool channel 44 passes through the inserted portion covering portion 18. The distal end portion of the channel tube 45 is connected to the cover distal end constituting portion 31, and thereby communicates with the channel distal end portion 42 provided in the cover distal end constituting portion 31. In the channel distal end portion 42, a treatment tool raising table 46 is pivotally provided to raise a treatment tool which has been sent through the treatment tool channel 44. A proximal end portion of the treatment tool raising table 46 is fixed to a rotary shaft 47 in such a manner that the treatment tool raising table 46 can be turned about the proximal end portion thereof in the channel distal end portion 42. A wire 48 is connected to the distal end portion of the treatment tool raising table 46. The raising table 46 can be raised or pulled down by pulling or pushing of the wire 48. In the raising wire 48 which passes through the inserted portion covering portion 18, a distal end portion thereof passes through a wire tube 49 connected to the cover distal end constituting portion 31, and a rear end thereof extends as far as the endoscope operating portion fixing port portion 33.

Although not shown, an endoscope inserting channel is provided in the inserted portion covering portion 18 substantially parallel to the channel tube 45 constituting the treatment tool channel 44, and the covered endoscope 4 is inserted into that endoscope inserting channel.

Figure 6:
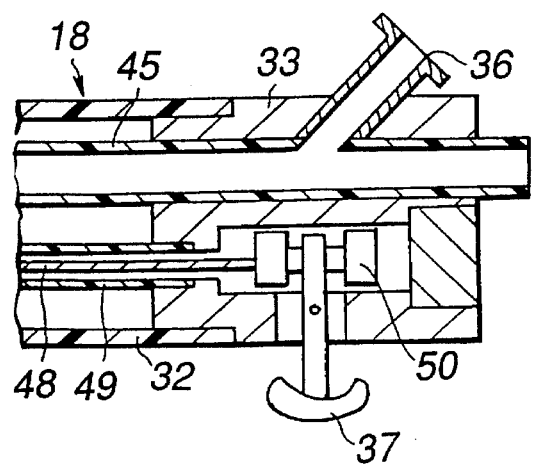
FIG. 6 is a cross-sectional view of a rear end portion of the endoscope cover of FIG. 2.

The rear end portion of the inserted portion covering portion 18 of the endoscope cover 3 has the structure shown in FIG. 6. The endoscope operating portion fixing port portion 33 provided at the rear end portion of the inserted portion covering portion 18 is connected to both the rear end portion of the channel tube 45 and the rear end portion of the wire tube 49. In the port portion 33, the channel tube 45 communicates with the treatment tool inserting port 36. A wire supporting member 50 is fixed to the rear end portion of the raising wire 48 which extends to the port portion 33 through the wire tube 49. The treatment tool raising lever 37 is coupled to the wire supporting member 50. The wire supporting member 50 can move back and forth in the port portion 33 within a predetermined range by the operation of the treatment tool raising lever 37.

Figure 7:
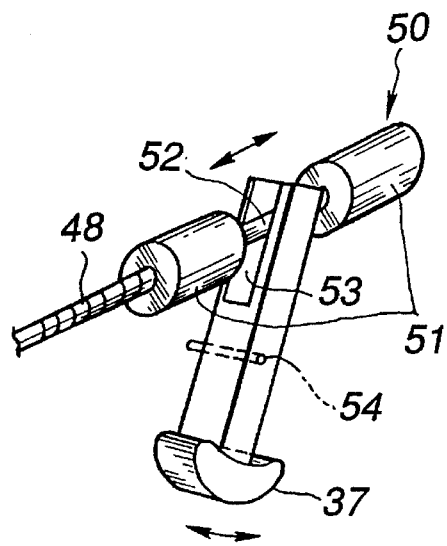
FIG. 7 is a perspective view of a treatment tool raising mechanism of the endoscope cover of FIG. 2.

FIG. 7 illustrates the structure of a treatment tool raising mechanism which includes the treatment tool raising lever 37 and the wire supporting member 50.

The wire supporting member 50 connected to the rear end portion of the raising wire 48 has large-diameter portions 51 and a small-diameter portion 52. A notched portion 53 is provided in the distal end portion of the raising lever 37. The small-diameter portion 52 of the wire supporting member 50 engages with the notched portion 53. The dimensions of the notched portion 53 and those of the small-diameter portion 52 are set such that they allow the notched portion 53 to engage with the small-diameter portion 52 with a clearance therebetween.

The treatment tool raising lever 37 is fixed in the port portion 33 in such a manner as to be pivotal about a rotary shaft 54. The operation of the raising lever 37 moves the distal end portion of the raising lever 37 within the small-diameter portion 52 of the wire supporting member 50. The moving raising lever 37 pushes the large-diameter portions 51 of the supporting member 50, and thereby drives the wire supporting member 50 in the two directions. Consequently, the raising wire 48 is pulled and loosened, and the treatment tool raising table 56 is thereby raised and pulled down in the distal end constituting portion 31.

In the first embodiment of the endoscope covered type endoscope apparatus 1, when used, the clean sterilized endoscope cover 3 is mounted on the covered endoscope 4. Therefore, the covered type endoscope 2 in which the covered endoscope 4 is separated from the external environment is inserted into the portion to be inspected, such as a body cavity. Thus, since the covered endoscope 4 is covered by the endoscope cover 3 and is not exposed during use, it is kept clean. Furthermore, a gas conduit, a liquid conduit and the treatment tool channel 44 are provided in the endoscope cover 3, and that endoscope cover 3 is discarded and a new sterilized endoscope cover 3 is put on the covered endoscope 4 after use. Therefore, reuse of the soiled conduits is prevented.

In the covered type endoscope 2 arranged in the manner described above, the covered endoscope 4, which is the endoscope body, can be kept clean without conducting washing and sterilization which would otherwise be conducted for each endoscopy, making endoscopy simplified. The covered endoscope 4 can be continuously used without re-washing or re-sterilization: washing and sterilization may be conducted on the covered endoscope, for example, once a day when all the inspections are completed. Therefore, the use efficiency of the endoscope is improved.

When various treatments are conducted using the treatment tools during endoscopy, the treatment tool to be used is inserted from the treatment tool inserting port 36 provided in the port portion 33 of the inserted portion covering portion 18, and is sent through the treatment tool channel 44. Thereafter, the distal end portion of the treatment tool is protruded from the channel open portion 35 in the cover distal end constituting portion 31, and is thereby reached to the desired portion for treatment.

The endoscope cover of this embodiment is used for the side-observing (side-viewing) endoscope, and is therefore provided with the treatment tool raising table for directing the distal end portion of the treatment tool toward the desired portion and the treatment tool raising device having the treatment tool raising mechanism.

When the treatment tool which has been inserted through the treatment tool channel 44 is raised or pulled down, the treatment tool raising lever 37 provided on the port portion 33 located on this side of the inserted portion covering portion 18 is operated to turn the raising lever 37 about the rotary shaft 54 and thereby move the wire supporting member 50 engaging with the distal end portion of the lever back and forth. Consequently, the raising wire 48 whose rear end portion is fixed to the wire supporting member 50 is pushed or pulled, and the treatment tool raising table 46 connected to the distal end portion of the raising wire 48 is thereby raised or pulled down.

Thus, since the treatment tool raising lever is provided at the proximal end portion of the inserted portion covering portion of the endoscope cover, i.e., close to the operating portion of the endoscope, when the endoscope cover is mounted on the covered endoscope, a complicated connection operation in which the raising wire of the treatment tool raising device is connected to the endoscope operating portion can be eliminated, thus improving the workability of the endoscope cover mounting operation.

A second embodiment of the present invention will be described below with reference to FIGS. 8 through 11.

The second embodiment relates to an endoscope cover used for the side-observing (side-viewing) endoscope, as in the case of the first embodiment.

A distal end constituting portion 61 of the endoscope cover has an endoscope distal end portion insertion hole 62 with which the distal end portion of the endoscope inserted into the endoscope insertion channel in the cover engages, and the channel distal end portion 42 which communicates with the treatment tool channel. The distal end portion of the treatment tool channel is open through a channel open portion 64. A cover glass 65 is provided in an observation open portion provided on the side of the endoscope distal end portion insertion hole 62 at a position corresponding to that of the observation and illumination windows of the inserted endoscope. The cover glass 65 separates the interior of the endoscope channel, including the endoscope distal end portion insertion hole 62, from the external environment, and assures the field of view of the endoscope.

A treatment tool raising table 66 is pivotally provided in the channel distal end portion 42 to raise the treatment tool which has been sent through the treatment tool channel. A raising wire 67 connected to the treatment tool raising table 66 extends to the endoscope operating portion fixing port portion of the endoscope cover (not shown). The rear end portion of the raising wire 67 is coupled to the treatment tool raising lever, as in the case of the first embodiment. The raising wire 67 is pushed or pulled by operating the treatment tool raising lever, and the treatment tool raising table 66 is thereby raised or pulled down in a direction indicated by an arrow in FIG. 8.

The structure of the distal end portion of the side-viewing type covered endoscope which is inserted into the endoscope cover will be described below with reference to FIGS. 9 and 10.

Figure 9:
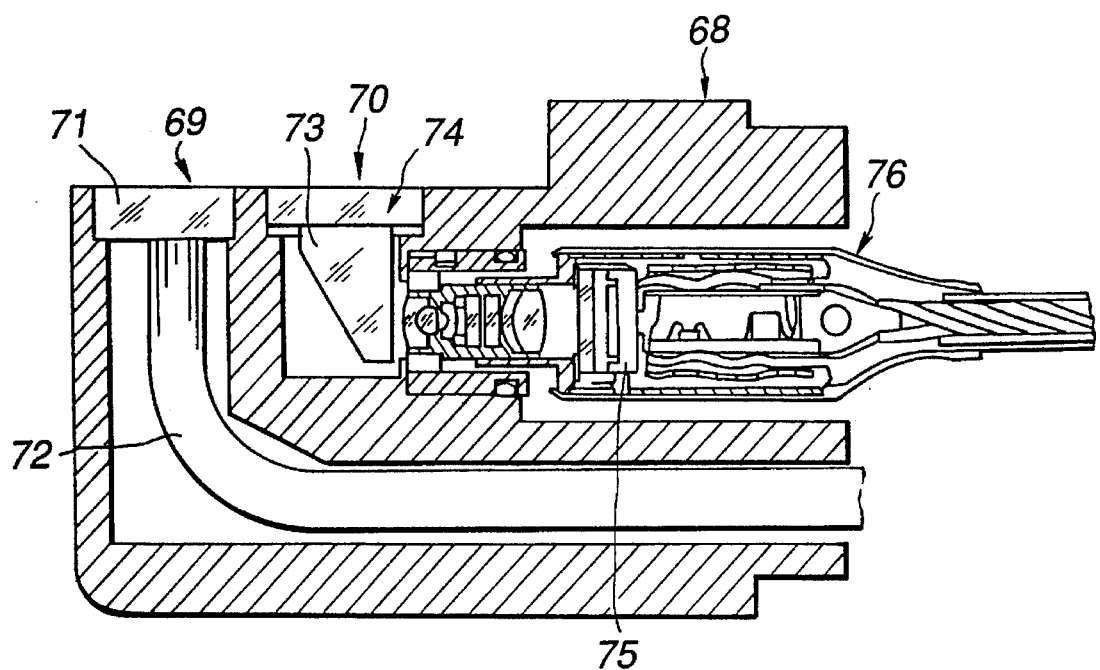
FIG. 9 is a longitudinal cross-sectional view of a distal end portion of a covered endoscope inserted into the endoscope cover of FIG. 8.

In a distal end portion 68 of the inserted portion of the covered endoscope, an illumination window 69 and an observation window 70 are disposed in such a manner that they are aligned in the axial direction of the inserted portion, as shown in FIG. 9. An illumination optical system 71 is disposed at the illumination window 69, and an emitting end of a light guide 72 which passes through the inserted portion is disposed behind the illumination optical system 71. An observation optical system 74, including a prism 73, is disposed at the observation window 70. An imaging unit 76 with a solid imaging element 75 is disposed behind the prism 73.

Figure 10:
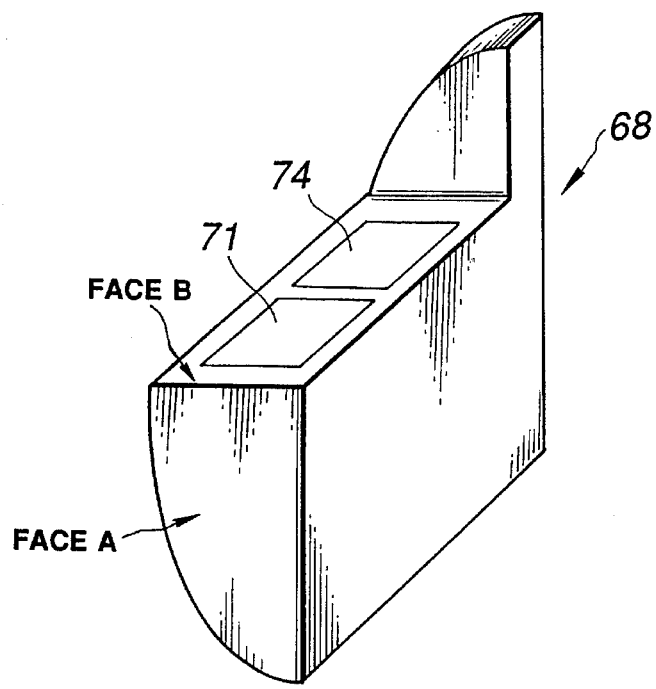
FIG. 10 is a perspective view of the distal end portion of the covered endoscope of FIG. 9.

The cross-sectional form of the distal end constituting portion 68 of the covered endoscope, taken in a direction perpendicular (transverse) to the axial direction of the inserted portion, is substantially semi-circular, as shown in FIG. 10. The distal end constituting portion 68 has a substantially semi-circular distal end surface (face A), and a side surface (face B), serving as the observation surface, which is substantially perpendicular to the axis in the longitudinal direction (hereinafter referred to as a longitudinal axis). On the face B are disposed the illumination optical system 71 and the observation optical system 74.

A rear end portion of the light guide 72 which passes through the universal cord 14 is connected to the light source unit 7. The illumination light from the light source unit 7 is transmitted to the distal end portion of the endoscope by the light guide 72, and the portion to be inspected is illuminated with the illumination light by the illumination optical system 71.

An image incident on a first lens disposed at the distal end of the observation optical system 74 is directed in a direction substantially perpendicular to the direction in which the image is incident by the prism 73, and then led to the imaging unit 76. In the imaging unit 76, the image of the object passes through the image forming optical system, and is formed on the image forming surface of the solid imaging element 75 which converts the formed image into an electric signal. The converted electric image signal is sent to the video processor 8 which performs various processings on the video signal. The processed signal is input to the monitor 11 which displays the image of the object on the display screen.

Figure 8:
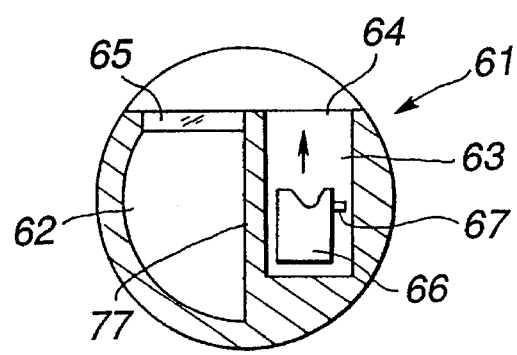
FIG. 8 is a lateral cross-sectional view of a distal end portion of an endoscope cover, showing a second embodiment of the present invention.

As shown in FIG. 8, the cross-sectional form of the endoscope distal end portion insertion hole 62 in the endoscope cover, taken in the direction perpendicular to the longitudinal axis of the inserted portion, is substantially semi-circular, and thus matches the cross-sectional form of the distal end portion of the covered endoscope inserted. In the distal end constituting portion 61 of the endoscope cover, the channel distal end portion 42 is provided parallel to the endoscope distal end portion insertion hole 62, and the treatment tool raising table 66 is disposed at a position substantially parallel to the longitudinal axis of the semi-circular cross-sectional form of the endoscope distal end portion insertion hole 62. The treatment tool raising table 66 is raised in a direction (indicated by the arrow in FIG. 8) substantially parallel to the longitudinal axis of the semi-circular cross-section of the endoscope distal end portion insertion hole 62.

In the above-described arrangement of the endoscope distal end portion insertion hole 62 of the endoscope cover, the treatment tool raising table 66, and the distal end constituting portion 68 of thee covered endoscope, since the treatment tool raising table 66 is located substantially parallel to the longitudinal axis of the semi-circular cross-section of the endoscope distal end portion insertion hole 62 (which is the longitudinal axis of the semi-circular distal end surface of the distal end constituting portion 68 of the endoscope), it can be located substantially parallel to the direction of the field of view of the observation optical system 74 of the endoscope, and the direction of the field of view of the endoscope thus corresponds to the direction in which the treatment tool is raised. This enables the operator to operate the treatment tool while checking the position thereof, thus improving the operability of the treatment tool, such as a clamp, and assuring safe and reliable treatment.

Furthermore, the endoscope distal end portion insertion hole 62 of the endoscope cover has a substantially semi-circular cross-sectional form and the treatment tool channel distal end portion is provided in an empty space which is not occupied by the endoscope distal end portion insertion hole parallel thereto, the space efficiency with which the components are disposed in the distal end portion of the endoscope cover having a channel is improved, and the diameter of the inserted portion of the covered type endoscope which employs the endoscope cover can thus be reduced.

Furthermore, since a partitioning wall 77 (see FIG. 8) between the endoscope distal end portion insertion hole 62 and the channel distal end portion 42 is reinforced by the insertion of the inserted portion of the covered endoscope 4, the treatment tool raising table 66 and the treatment tool placed on the raising table 66 can be raised or pulled down along the partitioning wall 77. Therefore, the partitioning wall 77 acts as the guide for the raising operation of the treatment tool raising table 66 and for the clamp or the like which is inserted into the treatment tool channel 44.

Figure 11:
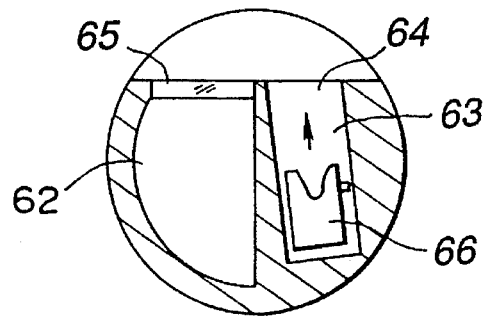
FIG. 11 is a cross-sectional view showing a modification of the second embodiment in which a direction in which a clamp raising table is raised in the distal end portion of the endoscope cover is changed from that shown in FIG. 8.

As the modification of the second embodiment, a distal end portion 78 of the endoscope cover may be formed such that the direction in which the treatment tool is raised is slightly inclined with respect to the direction of the field of view of the observation optical system of the endoscope, as shown in FIG. 11. In the distal end portion 78 of this modification, the treatment tool raising table 66 is provided in such a manner that it is raised in a direction slightly inclined with respect to the longitudinal axis of the semi-circular cross-section of the endoscope distal end portion insertion hole 62.

In this way, the direction in which the treatment tool is raised or pulled down by the treatment tool raising table 66 is slightly inclined with respect to the direction of the field of view of the observation optical system of the endoscope. Consequently, the treatment tool moves toward the center of the field of view of the endoscope, and the operation of the treatment tool, such as a clamp, is made easier.

Figure 12:
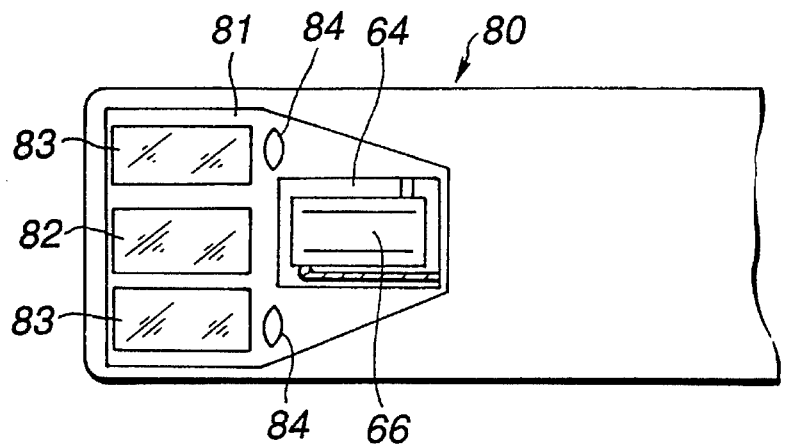
FIG. 12 is a side elevational view of the distal end portion of the endoscope cover, showing a third embodiment of the present invention.

A third embodiment of the present invention will be described below with reference to FIGS. 12 through 14.

The third embodiment is a modification of the distal end portion of the endoscope cover of the second embodiment. In this embodiment, a front direct-viewing endoscope is used, and the direction of the field of view is changed at the distal end portion of the endoscope cover mounted so that the front direct-viewing endoscope can be used as the side-viewing endoscope.

A distal end constituting portion 80 of the endoscope cover has a flat surface 81 on the side thereof and close to the distal end thereof. On the flat surface 81, an observation optical system 82 on the cover side and illumination optical systems 83 on the cover side are disposed in such a manner that they are aligned in a direction perpendicular to the axial direction of the inserted portion. The observation optical system 82 is sandwiched by the illumination optical systems 83. Gas/liquid nozzles 84 extend to the observation optical system 82 and the illumination optical systems 83 so as to allow the observation and illumination windows to be washed.

The channel open portion 64, which communicates with the treatment tool channel provided in the cover, is provided behind the observation illumination system 82 along the axial direction of the cover, and the clamp raising table 66 is disposed.

Figure 13:
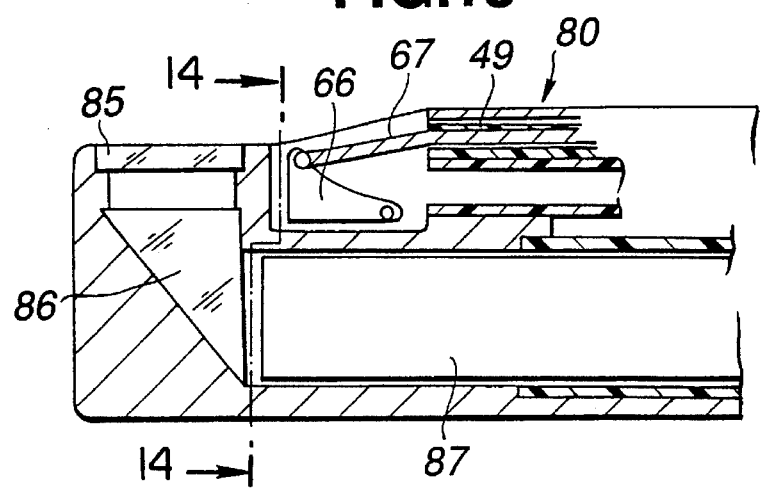
FIG. 13 is a longitudinal cross-sectional view of the distal end portion of the endoscope cover of FIG. 12.
Figure 14:
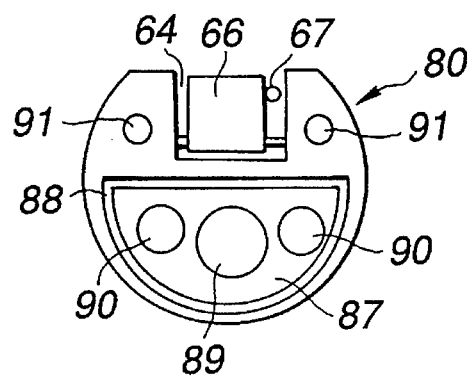
FIG. 14 is a section taken along the line 14—14 of FIG. 13.

The internal structure of the distal end constituting portion 80 of the endoscope cover will be shown in FIGS. 13 and 14.

Behind each of cover glasses 85 provided on the outer surface of the observation optical system 82 and the illumination optical systems 83, a prism 86 is disposed in order to change the direction of the illumination light or that of the light rays of an observed image in a direct-viewing type covered endoscope 87 by about 90°. The light rays direction changing means is not limited to the prism 86, and a reflecting member, such as a mirror, may also be employed. The provision of the prism 86 separately for each of the observation optical system 82 and the illumination optical systems 83 improves the optical performance.

An endoscope distal end portion insertion hole 88 of the endoscope cover has a substantially semi-circular cross-sectional form, as in the case of the second embodiment, and the substantially semi-circular distal end portion of the covered endoscope 87 is fitted into that insertion hole 88. The observation optical system 82 and the illumination optical systems 83 on the cover are disposed in such a manner that they respectively face an observation optical system 89 and illumination optical systems 90 of the covered endoscope 87. In addition, air/liquid conduits 91 which communicate with the air/liquid nozzles 84 are provided in the distal end constituting portion 80 of the endoscope cover.

The clamp raising table 66 is disposed above the central axis of the cross-section of the distal end constituting portion 80, i.e., above the covered endoscope 87 inserted into the cover, on an axis substantially parallel to the direction of the field of view. The raising wire 67 which passes through the wire tube 49 is connected to the clamp raising table 66.

When the observation and illumination optical systems and the endoscope distal end portion insertion hole are provided in the endoscope cover in the manner described above, side-viewing observation can be performed using the direct-viewing type covered endoscope. Also, selection between the direct-viewing and side-viewing observations can be made by selecting the endoscope cover with a channel.

When the treatment tool raising table is disposed in the manner described above, the distal end portion of the treatment tool which has passed through the channel can be located at the center of the field of view of the endoscope when raised, improving the operability of the treatment tool.

The method of assembling a treatment tool inserting port in the endoscope operating portion fixing port portion located at the rear end of the endoscope cover will be explained with reference to FIGS. 15 and 16.

In the rear end portion of the inserted portion covering portion 18 of the endoscope cover 3, the endoscope operating portion fixing port portion 33 is hermetically connected to the outer skin 32. The channel tube 45, the wire tube 49 and so on are inserted into the inserted portion covering portion 18. The rear end portion of the channel tube 45 is air-tight fixed to the port portion 33 by means of an adhesive or the like.

Figure 15:
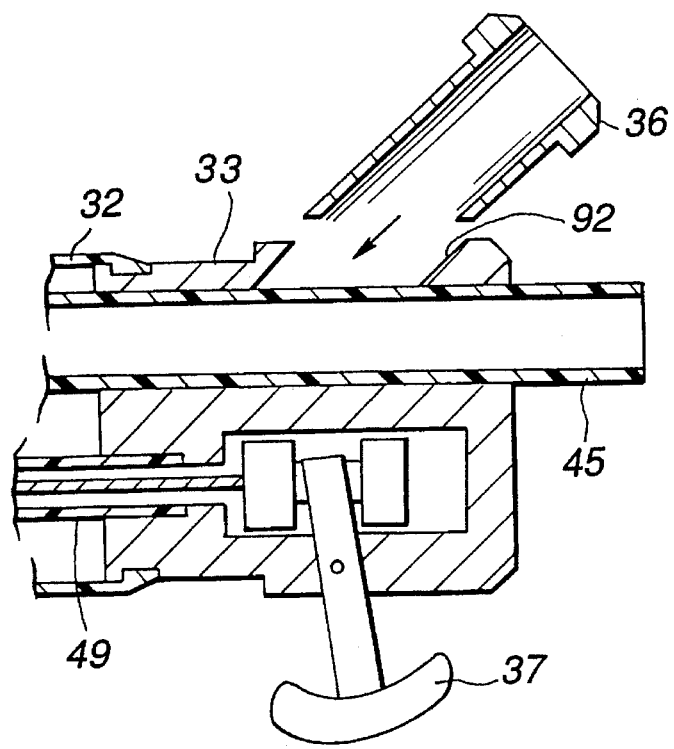
FIG. 15 is a cross-sectional view illustrating a first step of the method of assembling a treatment tool inserting port in an endoscope operating portion fixing port portion in a rear end portion of the endoscope cover.
Figure 16:
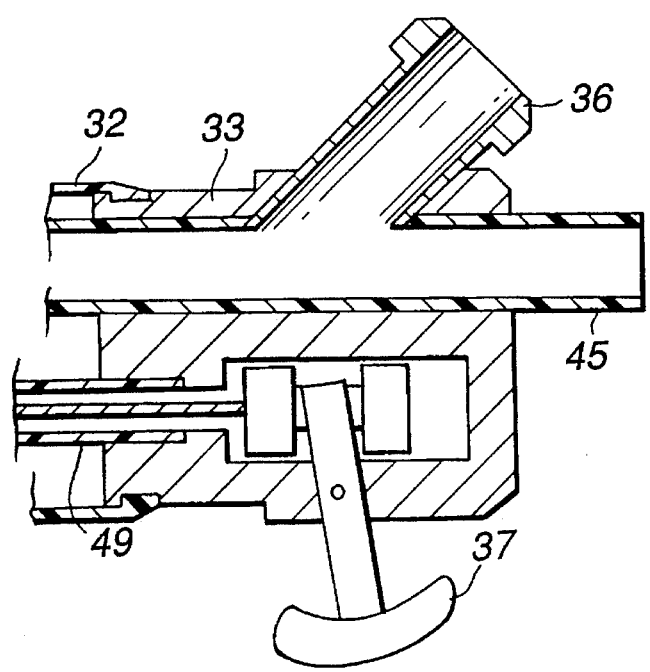
FIG. 16 is a cross-sectional view illustrating a second step of the method of assembling the treatment tool inserting port in the endoscope operating portion fixing port portion in the rear end portion of the endoscope cover.

For assembly, the channel tube 45 which has no open portion on the side thereof is first fitted into and adhered to the insertion hole of the port portion 33, as shown in FIG. 15. Thereafter, the portion of the channel tube 45 which closes an open portion 92 of the port portion 33 is opened from the open portion 92 corresponding to the treatment tool inserting port, and the treatment inserting port 36 is inserted into and fixed to the open portion 92, as shown in FIG. 16, whereby a clamp or the like can be inserted into the channel tube 45 from the treatment tool inserting port 36.

In this way, the need for opening a side hole in the channel tube 45 beforehand is eliminated. Since the hole for the treatment tool inserting port is opened after the channel tube 45 has been fixed to the port portion 33, alignment of the side hole in the channel tube 45 with the open portion 92 is omitted. Consequently, the workability of the assembly operation is improved.

Figure 17:
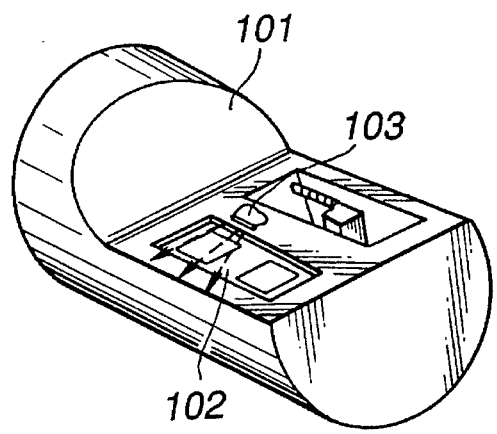
FIG. 17 is a perspective view of a distal end constituting portion showing the structure of gas/liquid conduits provided in the distal end constituting portion of the endoscope cover.
Figure 18:
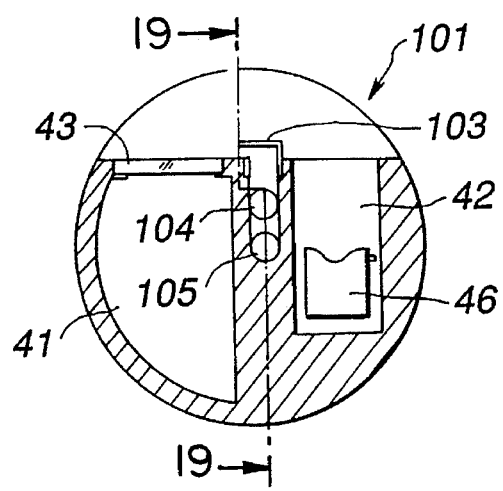
FIG. 18 is a lateral cross-sectional view of the distal end constituting portion of the endoscope cover of FIG. 17.
Figure 19:
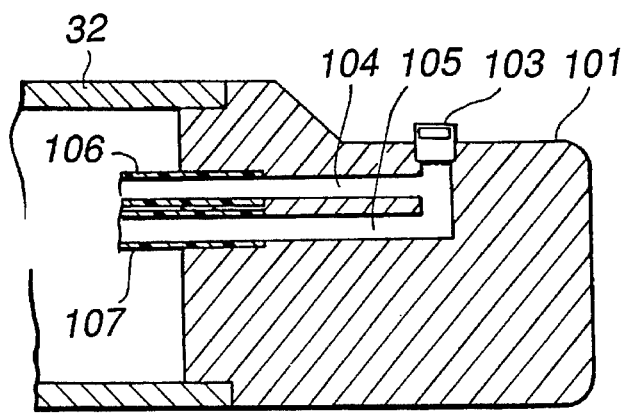
FIG. 19 is a cross-section taken along the line 19—19 of FIG. 18.

The structure of the gas/liquid conduit provided in the distal end constituting portion of the endoscope cover will be described below with reference to FIGS. 17 through 19. FIG. 17 is a perspective view of the distal end constituting portion. FIG. 18 is a lateral cross-sectional view of the distal end constituting portion. FIG. 19 is a cross-section taken along the line 19—19 of FIG. 18.

In a distal end constituting portion 101 of the endoscope cover, a gas/liquid nozzle 103 is provided close to the side portion of an observation open portion 102 so as to inject gas or liquid toward the observation and illumination windows of the observation open portion 102.

As shown in FIG. 18, a gas conduit 104 and a liquid conduit 105 are provided between the endoscope distal end portion insertion hole 41 and the channel distal end portion 42 parallel to the endoscope distal end portion insertion hole 41. The gas conduit 104 and the liquid conduit 105 are separated from each other in the longitudinal direction of the semi-circular cross-section of the endoscope distal end portion insertion hole 41 substantially parallel to each other. As shown in FIG. 19, the two conduits are combined at the distal end thereof to form an L-shaped single conduit, which communicates with the gas/liquid nozzle 103. The gas conduit 104 and the liquid conduit 105 are respectively connected to a gas tube 106 and a liquid tube 107, which are in turn connected to the fluid control unit.

To wash the observation and illumination windows, a washing fluid is sent from the fluid control unit to the gas and liquid conduits 104 and 105 by operating gas and liquid buttons (not shown) provided in the operating portion of the covered endoscope. The fluid which has been sent to the gas and liquid conduits 104 and 105 is ejected toward the observation and illumination windows from the gas/liquid nozzle 103.

Thus, since the fluid conduit, such as the gas conduit or the liquid conduit, is provided in the endoscope cover, the diameter of the inserted portion of the covered endoscope can be reduced. Furthermore, since the open portion of the fluid conduit, i.e., the open portion of the gas/liquid nozzle, is provided on the side of the open portion for observation, the fluid conduit is constituted by the conduit tubes, the L-shaped conduit hole and the nozzle alone, simplifying the conduit structure.

A fourth embodiment of %he present invention will be described below with reference to FIGS. 20 and 21.

In the fourth embodiment, the distal end portion of the treatment tool channel tube is curved in order to raise and pull down the treatment tool. Such a treatment tool channel tube acts as the treatment raising device provided in the distal end constituting portion of the endoscope cover.

Figure 20:
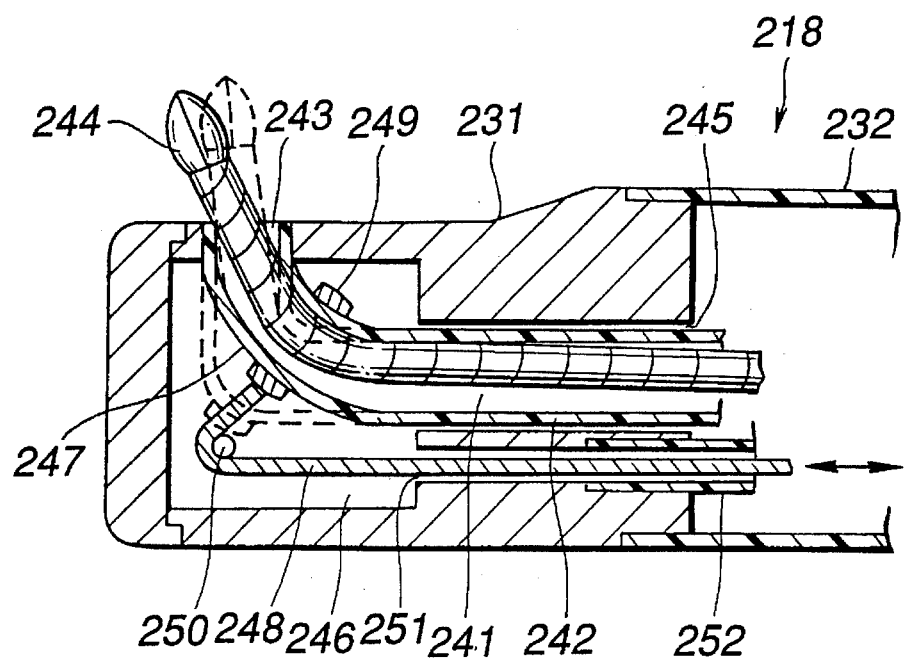
FIG. 20 is a cross-sectional view of a distal end portion of an endoscope cover showing a fourth embodiment of the present invention.

The structure of the distal end portion of an inserted portion covering portion 218 in the endoscope cover is shown in FIG. 20.

In the distal end portion of the inserted portion covering portion 218, a cover outer skin 232 is hermetically connected to a rear end of a distal end constituting portion 231 made of a hard resin. A channel tube 242, constituting a treatment tool channel 241, is inserted into the inserted portion covering portion 218. A channel open portion 243 provided at a distal end of the treatment tool channel 241 is open perpendicular to the axial direction of the endoscope cover. A treatment tool 244 which passes through the treatment tool channel 241 protrudes from that channel open portion 243 and reaches the desired portion for various treatments.

The channel tube 242 is made of a soft tube. The channel tube 242 passes through a channel guide hole 245 in the distal end constituting portion 231, extends into a channel rising chamber 246 with which the channel guide hole 245 communicates, and is then air-tight adhered to the channel open portion 243. In the channel rising chamber 246, the channel tube 242 has a curved portion 247 which is curved at about 90 degrees toward the channel open portion 243. The angle of protrusion of the treatment tool 244 changes by changing the curvature of the curved portion 247. In addition, since the channel tube 242 is not fixed relative to the channel guide hole 245, it is movable back and forth within the channel guide hole 245.

On the curved portion 247 of the channel tube 242 is provided a ring-shaped wire connecting member 249. The channel tube 242 is inserted into that ring-shaped wire connecting member. The wire connecting member 249 may be fixed or movable relative to the curved portion 247. A raising wire 248 is connected to the wire connecting member 249. The raising wire 248 is wound around a pulley member 250, serving as a wire guiding member fixed in the channel rising chamber 246, and then inserted into a wire guide hole 251 in the distal end constituting portion 231. A wire tube 252 is connected to the rear end of the wire guide hole 251. The raising wire 248 passes through the wire tube 252 and reaches the proximal end portion of the inserted portion covering portion 218.

Since the channel tube 242 is formed of a soft tube, the curved portion 247 of the channel tube 242 is pulled or loosened in the channel rising chamber 246 by pulling or pushing the raising wire 248 due to the force transmitted to the wire connecting member 249 from the wire 248, thereby changing the curvature of the curved portion 247 of the treatment tool channel. That is, in a treatment tool raising means of this embodiment, the angle of protrusion of the treatment tool (the angle at which the treatment tool is raised or pulled down) is changed by changing the curvature of the treatment tool channel by means of the raising wire 248, the wire connecting member 249 and the pulley member 250.

Figure 21:
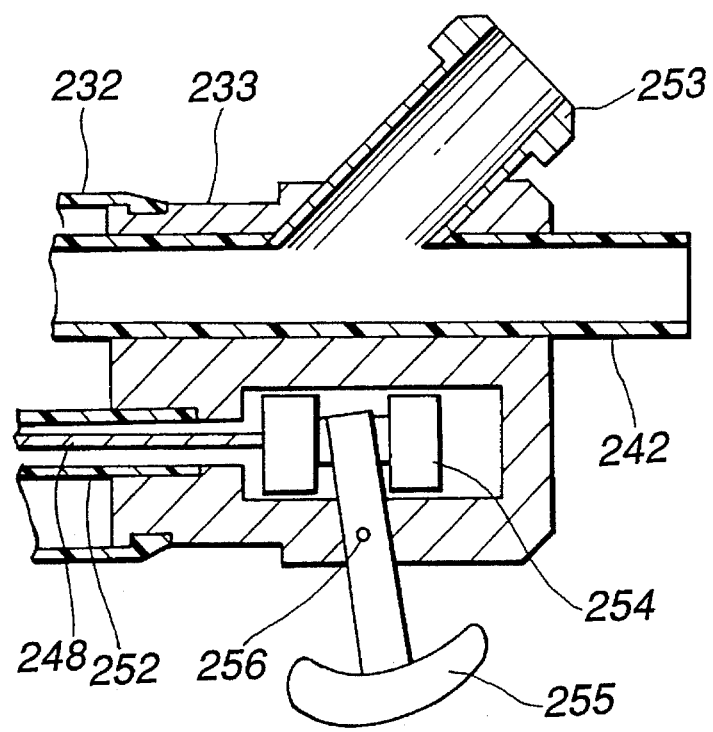
FIG. 21 is a cross-sectional view of a rear end portion of the endoscope cover of FIG. 20.

The structure of the rear end portion of the inserted portion covering portion is shown in FIG. 21.

In the rear end portion of the inserted portion covering portion 218, an endoscope operating portion fixing port portion 233 is provided for fixing the operating portion 13 of the covered endoscope 4. The port portion 233 is hermetically connected to the rear end portion of the cover outer skin 232. The endoscope operating portion fixing port portion 233 is connected to both the rear end portion of the channel tube 242 and the rear end portion of the wire channel 252. The channel tube 242 communicates with a treatment tool insertion port 253 in the port portion 233.

A wire supporting member 254 is fixed to the rear end portion of the raising wire 248 which passes through the wire channel 252 and extends to the port portion 233. A treatment tool raising lever 255 is coupled to the wire supporting member 254. When the treatment tool raising lever 255 is operated, it pivots about a rotary shaft 256, thereby moving the wire supporting member 254 back and forth in the port portion 233 within a predetermined range.

Although not shown, an endoscope inserting channel, into which the inserted portion 12 of the covered endoscope 4 is inserted, is provided in the inserted portion covering portion 218. The endoscope inserting channel, which is open at the rear end portion of the inserted portion covering portion 218, extends to the distal end constituting portion in a state in which it is maintained air-tight.

To perform various treatments with the treatment tool during endoscopy, the treatment tool to be used is inserted into the treatment tool channel 241 from the treatment tool inserting port 253 provided in the port portion 233 of the inserted portion covering portion 218, and is then sent through the treatment tool channel 241. The distal end of the treatment tool protrudes from the channel open portion 243 in the cover distal end constituting portion 231 and reaches the desired portion for treatment.

To raise or pull down the treatment tool which has been sent through the treatment tool channel 241, the treatment tool raising lever 255 provided in the port portion 233 located in the inserted portion covering portion 218 close to the operator is operated. Consequently, the raising lever 255 turns about the rotary shaft 256, and the wire supporting member 254 which engages with the distal end portion of the lever thereby moves back and forth. Consequently, the raising wire 248 whose rear end portion is fixed to the wire supporting member 254 is pushed or pulled, and the wire connecting member 249 connected to the distal end portion of the raising wire 248 in the channel rising chamber 246 is thereby pushed or pulled toward the pulley member 250. In consequence, the curved portion 247 of the channel tube 242 is pushed or pulled sideways, changing the curvature of the curved portion 247 and thereby changing the protrusion angle of the treatment tool which is inserted into the treatment channel 241. The treatment tool is raised or pulled down by such a treatment tool raising means.

In the case of a conventional standard endoscope which is subjected to sterilization for reuse, the treatment tool raising device provided therein must be able to be subjected to sufficient washing and sterilization and must have a durable structure so that it can withstand repetitive use. This requires a high processing technique for forming a treatment tool raising table and so on. Also, a complicated assembly operation, including the assembly of the treatment tool raising table or the like in the endoscope and connection of the treatment tool raising wire for transmitting the driving force from the treatment tool raising lever, is necessary, increasing the production cost.

In this embodiment, since the treatment tool raising means has a simpler structure than the treatment tool raising device which employs the treatment tool raising table and so on, the machining and assembly costs can be reduced, thus reducing the production cost.

Figure 22:
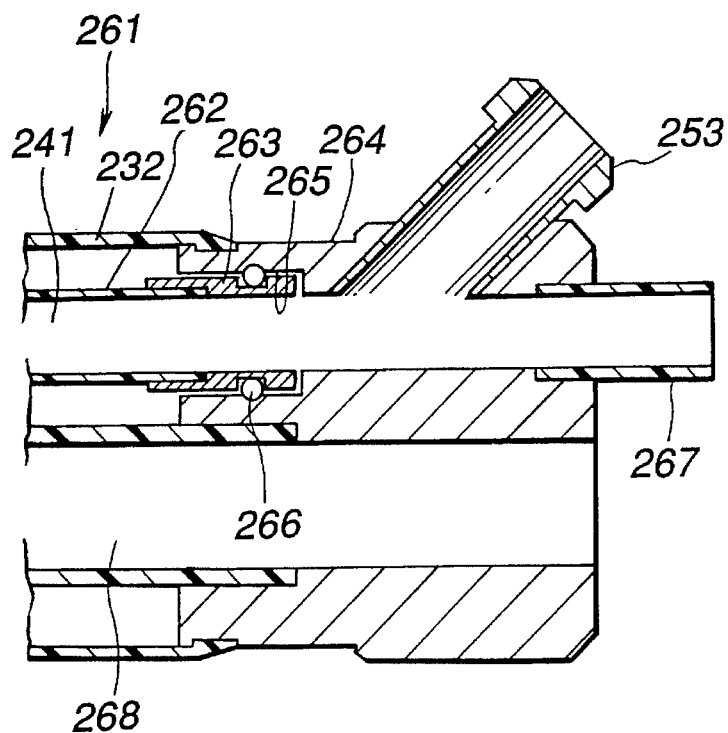
FIG. 22 is a cross-sectional view of a rear end portion of an endoscope cover showing a fifth embodiment of the present invention.

A fifth embodiment of the present invention will now be described with reference to FIG. 22. FIG. 22 is a cross-sectional view illustrating the structure of the rear end portion of the endoscope cover.

The fifth embodiment pertains to a channel tube for the treatment tool channel which is movable at the rear end portion of the cover.

In an endoscope cover 261 of this embodiment, a pipe-shaped channel supporting member 263 is fixed to the rear end portion of a channel tube 262 constituting the treatment tool channel 241 and which extends through the endoscope cover 261. The channel supporting member 263 is loosely fitted into a channel mounting recessed portion 261 formed in the endoscope operating portion fixing port portion 264 provided at the rear end portion of the endoscope cover 261, with a predetermined amount of clearance therebetween. Therefore, the channel supporting member 263 is slidable in both rotational and longitudinal directions relative to the port portion 264.

A sealing member 266, such as an O-ring, is provided between the channel supporting member 263 and the channel mounting recessed portion 265 in order to maintain the interior of the treatment tool channel 241 air-tight even when the channel supporting member 263 is caused to slide. A conduit tube 267 is connected to the rear end of the port portion 264. The conduit tube 267 is connected to the fluid control unit or the like as a suction conduit. In the endoscope cover 261, an endoscope inserting channel 268 into which the covered endoscope is inserted is provided. The endoscope inserting channel 268, which is open at the rear end portion of the port portion 264, extends over the endoscope cover 261 to the distal end constituting portion in an air-tight state.

Other structure, i.e, the structure of the distal end portion of the endoscope cover, is the same as that of the fourth embodiment, description thereof being omitted.

In this embodiment, the treatment tool raising wire is pushed or pulled to change the curvature of the curved portion of the channel tube distal end portion and thereby change the angle of protrusion of the treatment tool which has passed through the treatment tool channel 241 during the raising or pulling down operation of the treatment tool, as in the case of the fourth embodiment. At that time, since the rear end portion of the channel tube 262 is a free end which is movable relative to the port portion 264, even when the curvature of the curved portion of the channel tube is changed or when the inserted portion of the endoscope cover into which the endoscope is inserted is curved or twisted, the channel supporting member 264 is freely moved in the rotational and longitudinal directions, and twist of the channel tube 262 is thus prevented.

Thus, deterioration in the inserting property of the treatment tool and deterioration in the curved portion operability, caused by twist of the treatment tool channel tube in the endoscope cover, can be prevented. Consequently, the treatment tool can be smoothly inserted, and the durability of the treatment tool channel or the like can be improved.

Now, the structure of an auxiliary endoscope inserting tool provided at the rear end portion of the inserted portion covering portion of the endoscope cover will be explained.

Figure 23:
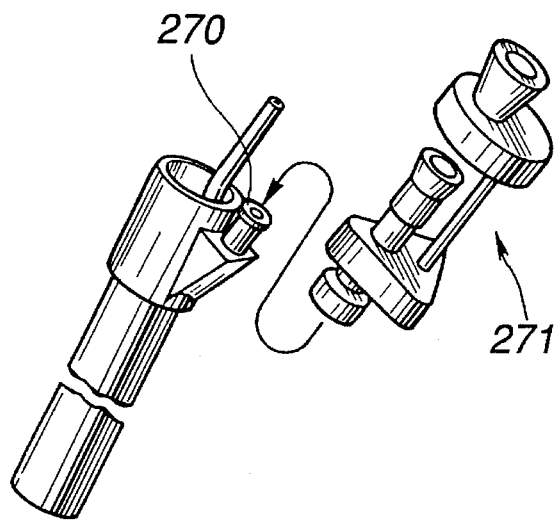
FIG. 23 is a perspective view of a conventional standard auxiliary endoscope inserting tool.

In the case of, for example, a double scope type endoscope apparatus in which a small-diameter endoscope or the like is inserted into the treatment tool channel, an auxiliary endoscope inserting tool is provided at the treatment tool inserting port as the guide for insertion of the small-diameter endoscope. Generally, an auxiliary endoscope inserting tool 271, such as that shown in FIG. 23, is used. This tool 271 is detachably mounted on a treatment tool inserting port 270 of, for example, a large-diameter endoscope or endoscope cover, and is washed, sterilized or disinfected repeatedly for reuse. Such an auxiliary endoscope inserting tool 271 has a complicated structure and hence it takes much time and trouble for the tool to be washed, sterilized or disinfected.

Therefore, if the auxiliary endoscope inserting tool is formed at the rear end portion of the endoscope cover integrally with the endoscope cover and if the auxiliary endoscope inserting tool is discharged together wih the endoscope cover after use, the need for sterilizing and disinfecting the auxiliary endoscope inserting tool is eliminated, improving the use efficiency of the endoscope.

Figure 24:
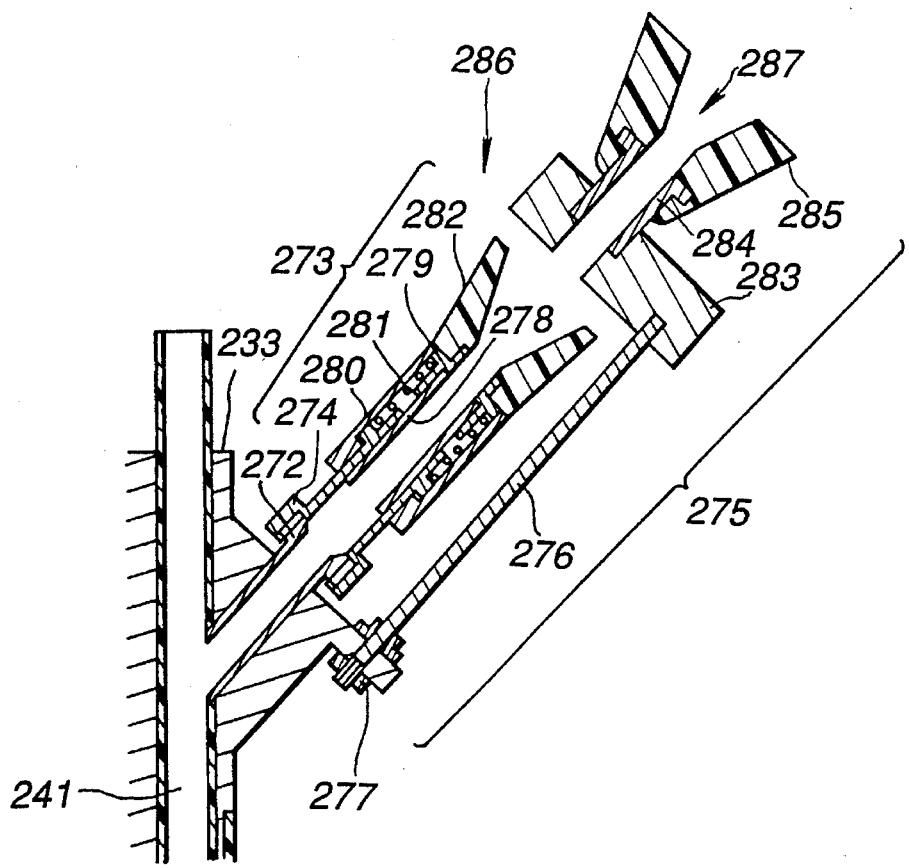
FIG. 24 is a cross-sectional view of an auxiliary endoscope inserting tool provided integrally with the rear end portion of the endoscope cover.

An example of such an auxiliary endoscope inserting tool provided integrally with the endoscope cover is shown in FIG. 24.

In the endoscope operating portion fixing port portion 233 provided at the rear end portion of the inserted portion covering portion of the endoscope cover, a treatment tool inserting port 272 is provided on the side thereof in such a manner that it communicates with the treatment tool channel 241. The outer peripheral portion of the distal end portion of the treatment tool inserting port 272 is threaded, and an auxiliary inserting tool front set 273 is mounted on that threaded portion. A mounting member 274 whose inner peripheral portion is threaded is provided at one end of the auxiliary inserting tool front set 273. The mounting member 274 is threadedly engaged with the treatment tool inserting port 272, whereby the auxiliary inserting tool front set 273 is mounted on the treatment tool inserting port 272. A supporting member 276 for an auxiliary inserting tool rear set 275 is fixedly screwed to the vicinity of the auxiliary inserting tool front set 273.

In the auxiliary inserting tool front set 273, a cylindrical sliding guide member 278 and a front base 279 are provided on the distal end side of the mounting member 274. A coming-off preventing member 280 is provided on the mounting member 274, the slide guide member 278 and the outer peripheral portion of the front base 279, and a spring member 281 is provided between the mounting member 274 and the front base 279 to urge the front base 279 toward the distal end thereof. An endoscope inserted portion retaining member 282, made of an elastic member, is provided at the end portion of the front base 279 in order to retain the inserted portion of the small-diameter endoscope. In the auxiliary inserting tool front set 273 arranged in the manner described above, the endoscope inserted portion retaining member 282, the front base 279 and so on are slidable in the axial direction of the front set along the mounting member 274.

In the auxiliary inserting tool rear set 275, a rear body 283 is provided at the distal end portion of the supporting member 276, and a rear base 283 and an endoscope inserted portion breakage preventing member 285 are mounted on the rear body 283 in that order.

An auxiliary endoscope inserting tool 286 consisting of the auxiliary inserting tool front set 273 and the auxiliary inserting tool rear set 275 is arranged in such a manner that the center of the treatment tool inserting port 272, the center of the auxiliary inserting tool front set 273 and the center of the auxiliary inserting tool rear set 275 substantially coincide with each.

To insert the small-diameter endoscope into the treatment tool channel 241, the inserted portion of the endoscope is inserted from the inserting port 287 of the auxiliary inserting tool rear set 275 through the auxiliary inserting tool front set 273, the treatment tool inserting port 272 then into the treatment tool channel 241. The distal end of the inserted portion of the endoscope is protruded from the channel open portion in the distal end constituting portion of the endoscope cover. At that time, the operator grips the endoscope inserted portion retaining member 282 of the auxiliary inserting tool front set 273 by hand and thereby retains the small-diameter endoscope while moving the auxiliary inserting tool front set 273 back and forth to insert the inserted portion of the endoscope into the treatment tool channel.

Thus, since the auxiliary endoscope inserting tool of this embodiment is provided integrally with the port portion of the endoscope cover, it can be replaced together with the endoscope cover after use. Therefore, the need for sterilizing and disinfecting the auxiliary inserting tool for each use is eliminated while the double scope covered type endoscope apparatus can be kept clean. In addition, since the auxiliary inserting tool front set 273 and the auxiliary inserting tool rear set 275 can be removed from the treatment tool inserting port, when necessary, an ordinary treatment tool may be able to be inserted into the channel.

The distal end constituting portion and the port portion of the endoscope cover with the channel, shown in FIGS. 20 and 21, may be formed of a resin, such as polysulfone. The cover outer skin of the endoscope cover may be made of polytetrafluoroethylene (PTFE). Bismuth oxide is added to such polysulfone or PTFE.

An endoscope cover formed of polysulfone or PTFE has a high chemical resistance. Bismuth oxide is a substance which is highly resistance to X-rays and is thus used in drainage tubes or the like. An endoscope cover made of polysulfone or PTFE to which bismuth oxide is added thus has a high X-ray resistance. In an endoscope cover having high chemical and X-ray resistances, breakage can be prevented during the use of the covered type endoscope.

Figure 25:
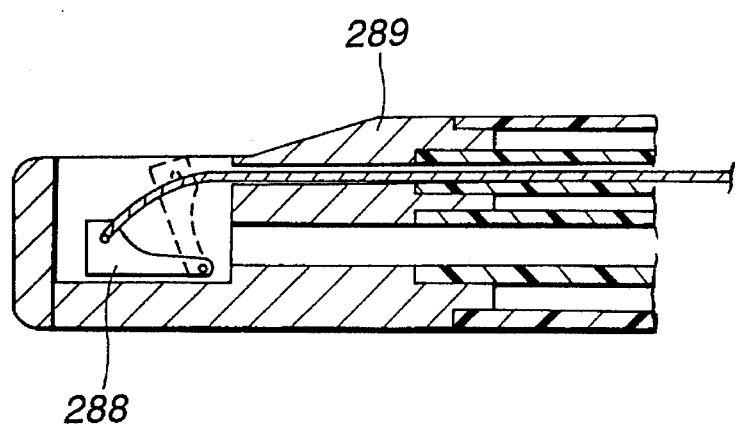
FIG. 25 is a cross-sectional view showing a modification in which the distal end portion of the endoscope cover is formed of an insulating material.

Regarding the distal end constituting portion of the endoscope cover, an insulating material may be used to form the distal end constituting portion 231 shown in FIG. 20. An insulating material may also be used to form a distal end constituting portion 289 with a treatment tool raising table 288, shown in FIG. 25. The distal end constituting portion 289 may be made of a resin, such as polysulfone or modified polyphenylene oxide, or a ceramic.

If the distal end constituting portion of the endoscope cover, i.e., the peripheral portion of the channel open portion, is made of an insulating material, when a high-frequency treatment is performed using the treatment tool inserted, leakage of the high-frequency signal to the peripheral portion of the channel open portion can be prevented, and a safer treatment can thus be performed.

Figure 26:
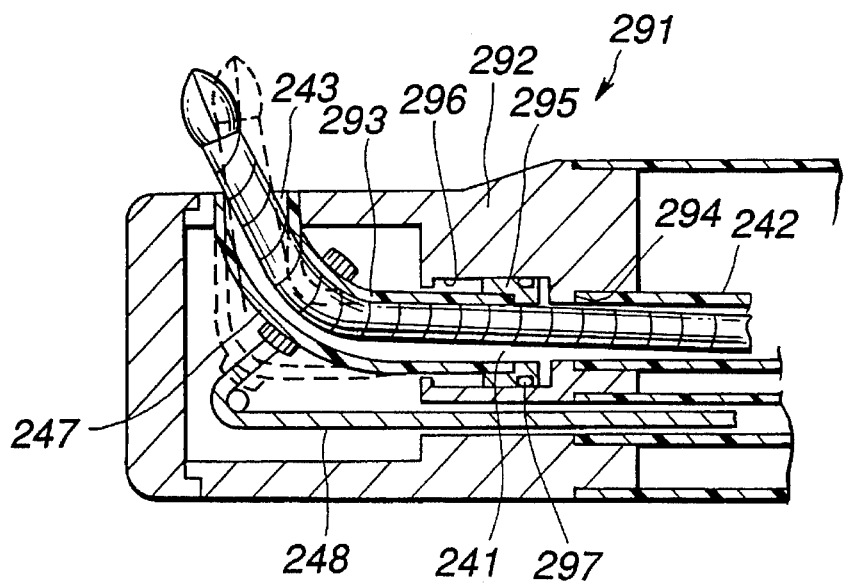
FIG. 26 is a cross-sectional view of a distal end, portion of an endoscope cover showing a sixth embodiment of the present invention.

A sixth embodiment of the present invention will be described below with reference to FIG. 26. FIG. 26 is a cross-sectional view showing the structure of the distal end portion of an endoscope cover.

The sixth embodiment is a modification of the fourth embodiment, and pertains to a treatment tool channel tube which is movable in the distal end constituting portion of the endoscope cover.

In an endoscope cover 291, the channel tube 241 is made up of the channel tube 242 which extends from the rear end portion of a distal end constituting portion 292 to the rear end portion of the cover, and a distal end channel tube 293 movably mounted at one end thereof.

The channel tube 242 is inserted into and fixed to a tube mounting shoulder portion 294 in the rear end portion of the distal end constituting portion 292. One end of the distal end channel tube 293 is fixed to the channel open portion 243. The intermediate portion of the distal end channel tube 293 forms the curved portion 247. The other end thereof, to which a pipe-shaped channel supporting member 295 is fixed, is loosely fitted into a channel guide 296 provided in front of the tube mounting shoulder portion 294 with a predetermined amount of clearance therebetween. A sealing member 297, such as an 0-ring, is disposed between the channel supporting member 295 and the channel guiding hole 296. The channel supporting member 295 is slidable relative to the distal end constituting portion 292 in a state wherein the interior of the treatment tool channel is maintained watertight.

The other structure is the same as that of the fourth embodiment, description thereof being omitted.

To raise or pull down the treatment tool which has been sent through the treatment tool channel 241, the raising wire 248 is pushed or pulled in the same manner as that of the fourth embodiment. Consequently, a distal end channel tube 293 is pushed or pulled sideways, and the curvature of the curved portion 276 is thereby changed, changing the angle of protrusion of the treatment tool. At that time, as the distal end channel tube 293 is curved, the channel supporting member 296 which is one free end of the distal end channel tube 293 slides back and forth in a state where the interior of the channel is maintained watertight.

When the channel tube is curved by the pulling or pushing of the raising wire which is performed to raise or pull down the treatment tool, a tensile force is applied to the channel tube. However, in this embodiment, the tensile force applied can be absorbed by sliding of the distal end channel tube 293, application of an excessive load to the channel tube can be prevented. Thus, the durability of the channel tube is improved.

To absorb the tensile force applied to the channel, part of the channel tube may be formed of bellows. Alternatively, the channel tube may be formed of a highly elastic and expandable material.

A seventh embodiment of the present invention will be described below with reference to FIGS. 27 and 28.

The seventh embodiment is a modification of the fifth embodiment, and relates to a movement restricting means for the treatment tool channel tube.

In an endoscope cover 301 of the seventh embodiment, a pipe-shaped channel supporting member 302 is fixed to the rear end portion of the channel tube 262, as in the case of the fifth embodiment. The channel supporting member 302 is loosely fitted into a channel mounting recessed portion 304 provided in an endoscope operating portion fixing port portion 303 provided at the rear end portion of the endoscope cover 301 with a predetermined amount of clearance between the channel supporting member 302 and the channel mounting recessed portion 304. The channel supporting member 302 is slidable in a rotation direction relative to the port portion 303.

Figure 27:
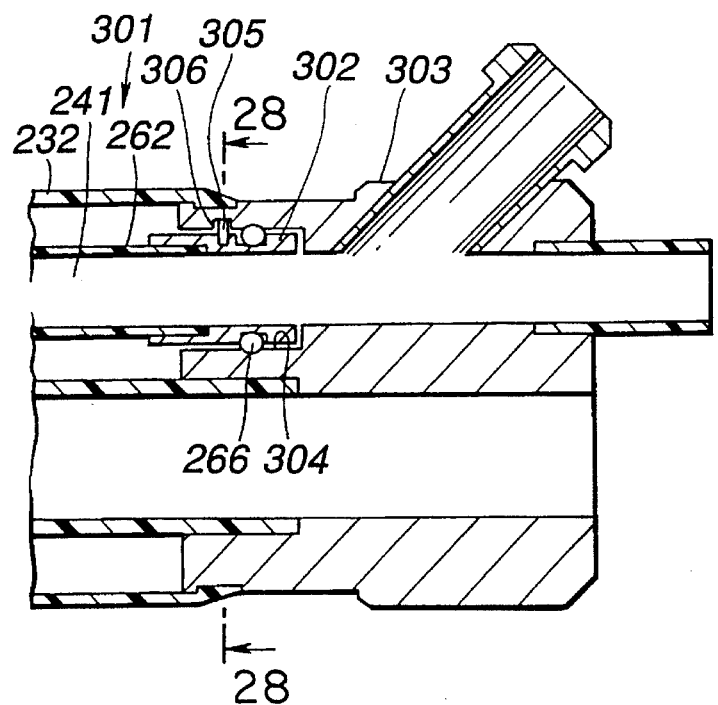
FIG. 27 is a cross-sectional view of a rear end portion of an endoscope cover showing a seventh embodiment of the present invention.
Figure 28:
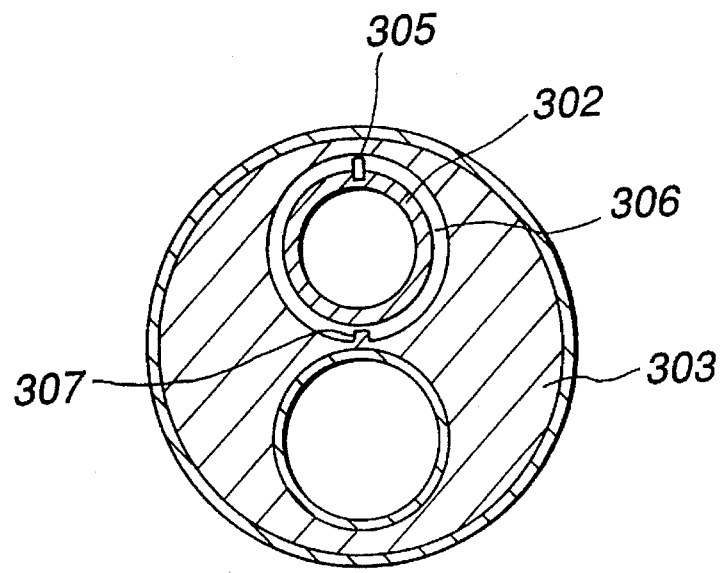
FIG. 28 is a cross-section taken along the line 28—28 of FIG. 27.

A position restricting pin 305 protrudes from the side of the channel supporting member 302 into a rotation guide groove 306 formed in a circumferential direction, as shown in FIGS. 27 and 28. The position restricting pin 305 is movable in the rotation guide groove 306. In the rotation guide groove 306, a stopper 307 protrudes in a peripheral direction to restrict the amount of rotation of the channel supporting member 302.

The other structure is the same as that of the fifth embodiment, description thereof being omitted.

The provision of the channel tube movement restricting means, made up of the position restricting pin 305, the rotation guide groove 306 and the stopper 307, enables the amount of rotation of the channel supporting member 302 provided at the end portion of the channel tube to be restricted, preventing crushing of the treatment tool channel, which would be caused by an excessive twist thereof.

An eighth embodiment of the present invention will be described below with reference to FIGS. 29 and 30.

The eighth embodiment is also a modification of the fifth embodiment, and relates to the provision of a movement restricting means for the treatment tool channel tube.

In an endoscope cover 311 of the eighth embodiment, the pipe-shaped channel supporting member 302 is fixed to the rear end portion of the channel tube 262, as in the case of the fifth embodiment. The channel supporting member 302 is loosely fitted into a channel mounting recessed portion 313 provided in an endoscope operating portion fixing port portion 312 provided at the rear end portion of the endoscope cover 311 with a predetermined amount of clearance between the channel supporting member 302 and the channel mounting recessed portion 313. The channel supporting member 302 is slidable in the longitudinal direction of the channel tube relative to the port portion 312.

Figure 29:
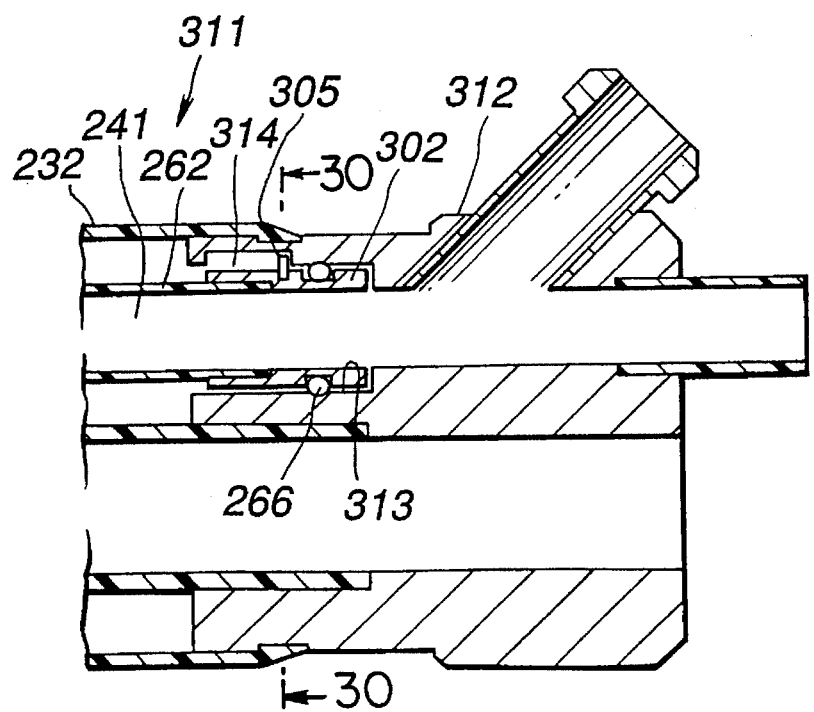
FIG. 29 is a cross-sectional view of a rear end portion of an endoscope cover showing an eighth embodiment of the present invention.
Figure 30:
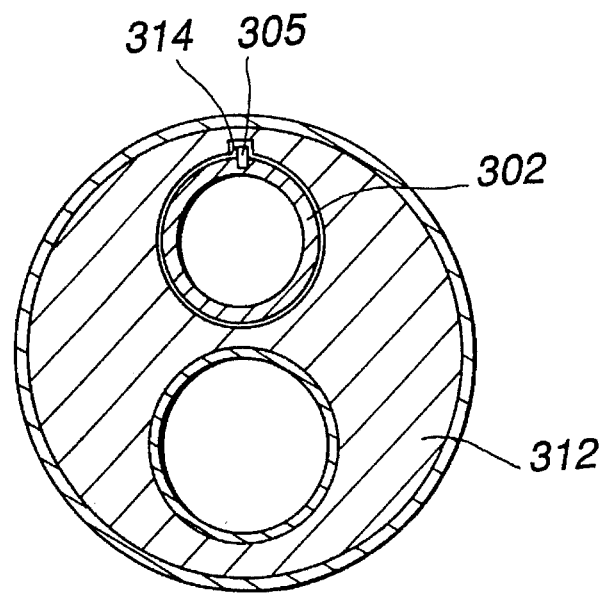
FIG. 30 is a cross-section taken along the line 29—29 of FIG. 29.

The position restricting pin 305 protrudes from the side of the channel supporting member 302 into a stroke guide groove 314 formed in the longitudinal direction substantially in a straight line form, as shown in FIGS. 29 and 30. The position restricting pin 305 is movable in the stroke guide groove 314.

The other structure is the same as that of the fifth embodiment, description thereof being omitted.

The provision of the channel tube movement restricting means, made up of the position restricting pin 305 and the stroke guide groove 314, enables the amount of movement of the channel supporting member 302 provided at the end portion of the channel tube to be restricted in the axial direction thereof, preventing breakage of the treatment tool channel, which would be caused by an excessive tensile force applied to the channel tube.

Furthermore, deformation or breakage of the treatment tool channel, caused by an external force applied thereto, can be more effectively prevented by providing a combination of the movement restriction means in the rotational direction according to the seventh embodiment and the stroke restriction means in the axial direction according to the eighth embodiment.

A ninth embodiment of the present invention will be described below with reference to FIGS. 31 through 36.

The ninth embodiment relates to the structure of a fluid conduit for gas or liquid or of a channel tube which forms a treatment tool channel.

Figure 31:
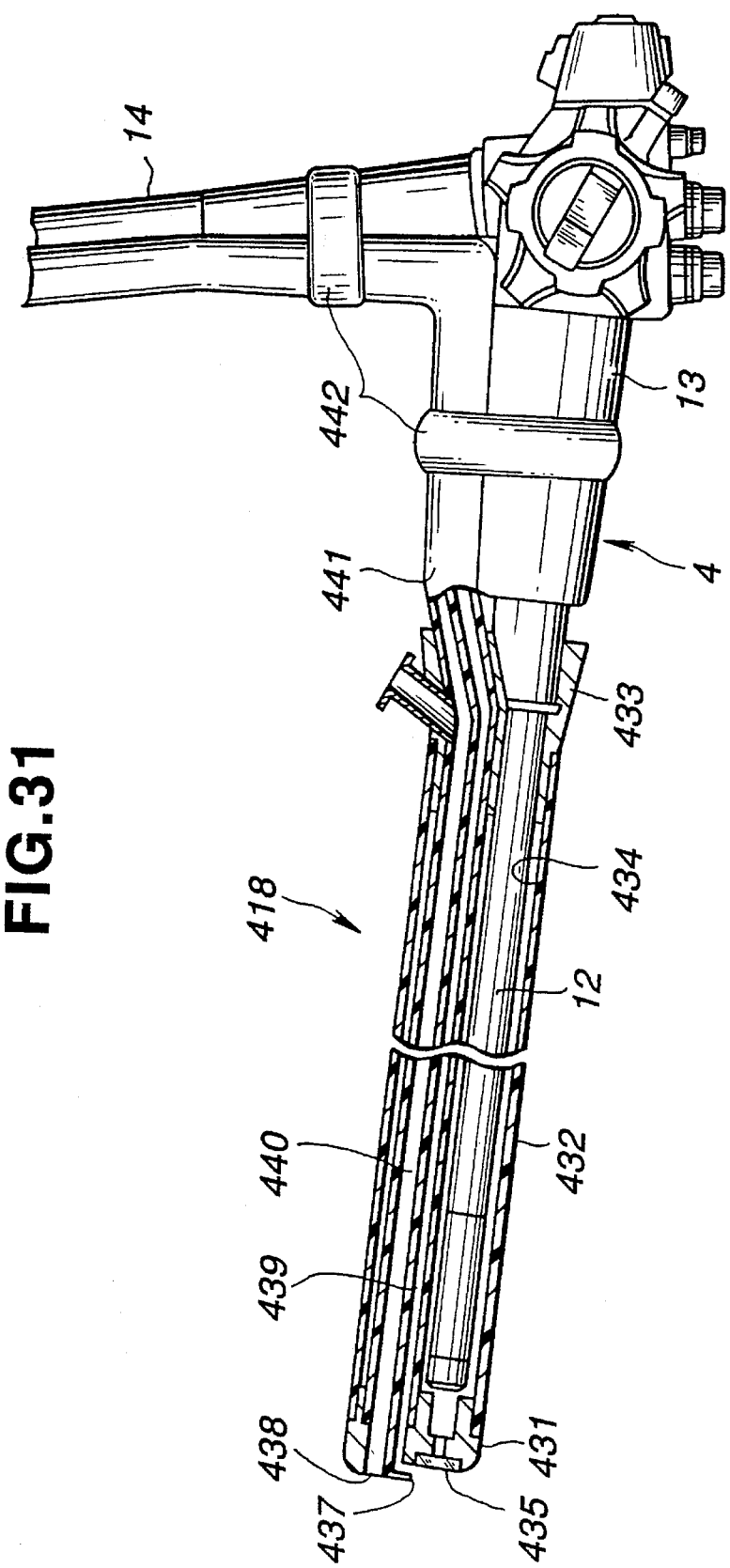
FIG. 31 illustrates how a ninth embodiment of an endoscope cover with a channel according to the present invention is mounted on the covered endoscope.

FIG. 31 illustrates how an inserted portion covering portion 418 of an endoscope cover according to the ninth embodiment is mounted on the covered endoscope 4.

In the inserted portion covering portion 418, a cover distal end constituting portion 431, a cover outer skin 432 and an endoscope operating portion fixing port portion (hereinafter referred to as a port portion) 433 for fixedly connecting the operating portion 13 of the endoscope are hermetically connected with each other in that order with the cover distal end constituting portion 431 located on the distal end of the inserted portion covering portion 418. The inserted portion 12 of the covered endoscope 4 is inserted into an endoscope inserting channel 434 provided in the inserted portion covering portion 418 so as to allow the covered endoscope 4 to be separated from the external environment.

Figure 32:
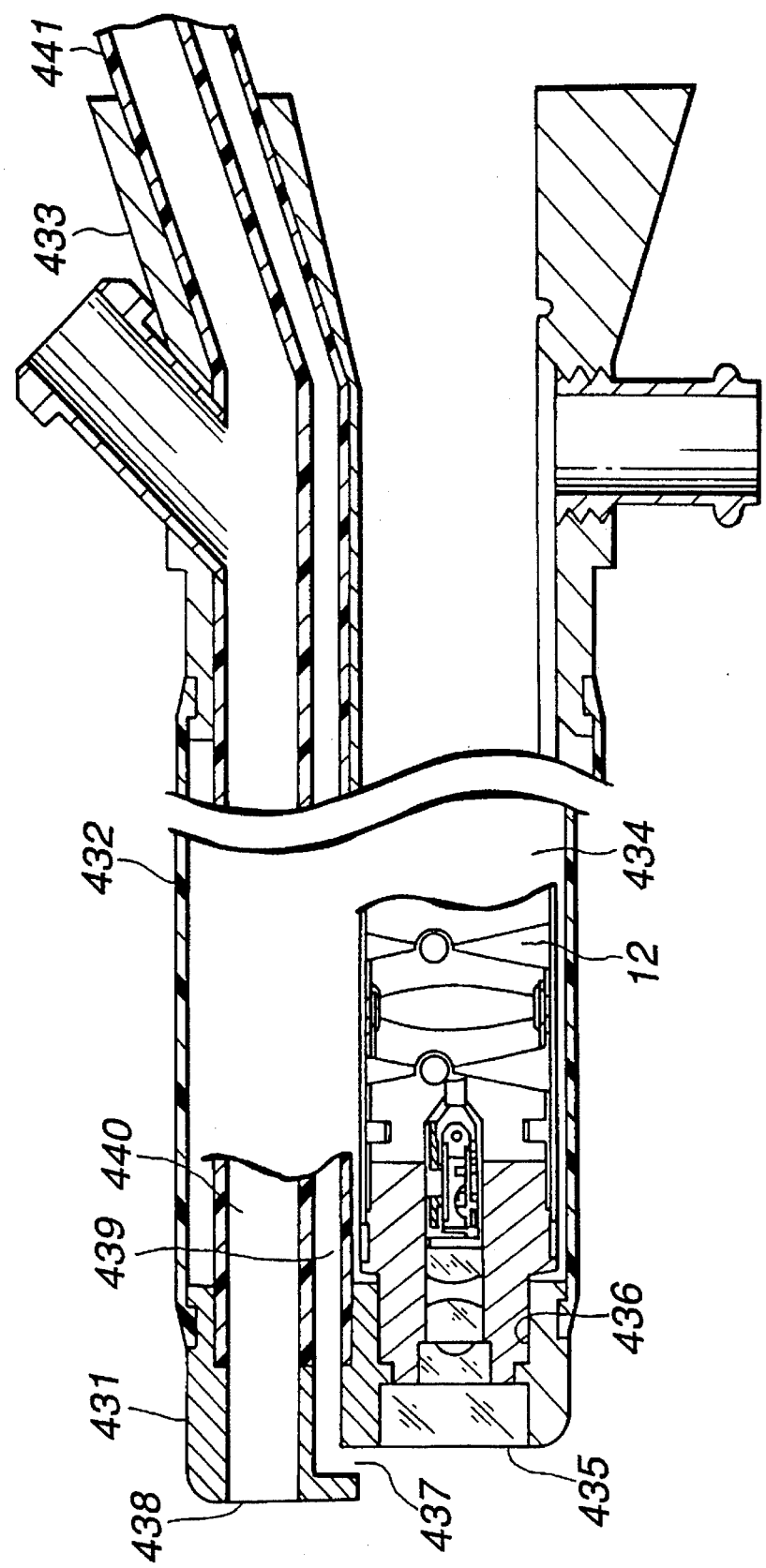
FIG. 32 is a cross-sectional view of an endoscope cover.

As shown in FIGS. 31 and 32, a transparent cover glass 435 is disposed in the cover distal end constituting portion 431 in such a manner that it opposes the observation and illumination windows of the covered endoscope 4. Therefore, the field of view of the observation optical system provided on the distal end portion of the covered endoscope, which is fitted into an endoscope distal end portion inserting hole 436, is obtained without the observation optical system being soiled, and irradiation of the illumination light toward the portion to be inspected and observation of the portion to be inspected are thus enabled.

In the distal end constituting portion 431 are also provided a gas/liquid nozzle 437 for injecting a washing fluid toward the cover glass 435 and a channel open portion 438 for the treatment tool channel in which a treatment tool is inserted. The gas/liquid nozzle 437 communicates with a gas/liquid tube 439, and the channel open portion 438 communicates with a treatment tool channel tube 440.

The gas/liquid tube 439 and the treatment tool channel tube 440 form a multi-lumen tube 441 having a plurality of channels as conduit channels. The multi-lumen tube 441 extends toward the port portion 433 as a single tube. The multi-lumen tube 441 may be made of urethane, drawn polytetrafluoroethylene or polyvinyl chloride. The multi-lumen tube 441 passes through the port portion 433 in a rearward direction from the distal end side of the inserted portion covering portion toward the operating portion 13 of the endoscope.

The portion of the multi-lumen tube 441 which protrudes from the rear end portion of the port portion 433 extends along the operating portion 13 of the endoscope and universal cord 14 while being fixed thereto at several position thereof with band members 442. The rear end portion of the multi-lumen tube 441 is connected to the fluid control unit 9 for gas/liquid injection or suction.

Figure 33:
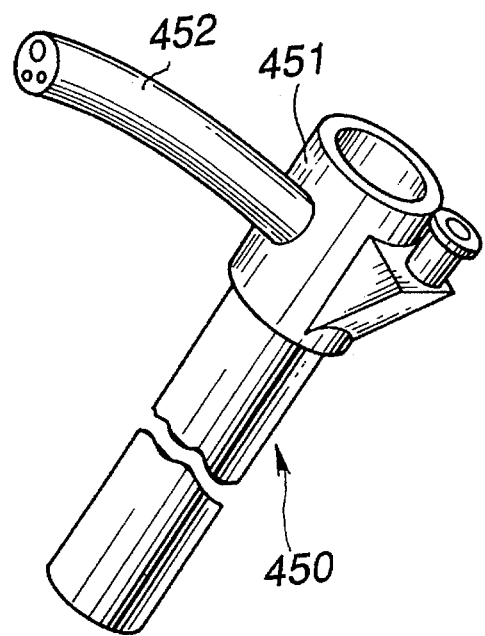
FIG. 33 is a perspective view of a conventional standard endoscope cover with a conduit tube.

A conduit tube which communicates with the channel provided in the endoscope cover extends from the rear end portion of the endoscope cover and is connected to the fluid control unit or the like. A conventional conduit tube connection structure may be arranged in the manner described below: a conduit tube 452 extends from the side surface portion of an endoscope operating portion fixing port portion 451 at the rear end portion of an endoscope cover 450, as shown in FIG. 33. In such a conventional structure, the conduit tube 452 is provided at a position separated from the operating portion of the covered endoscope which is fixed to the endoscope operating portion fixing port port 451, and a plurality of cords or tubes, including the universal cord, extend from the endoscope operating portion, disturbing the operation of the endoscope.

In this embodiment, the conduit tube which forms the gas/liquid conduit, the suction conduit and the treatment tool channel and so on is provided in the form of the multi-lumen tube 441, and the rear end side of the multi-lumen tube 441 which extends from the rear end portion of the port portion 433 is fixed to the operating portion of the endoscope of the like by means of the band members 442.

Thus, since the multi-lumen tube 441 which acts as the conduit tube passes through the port portion 433 and extends toward the operating portion 13 of the endoscope, it can be readily fixed to the operating portion 13 or the like. Therefore, the multi-lumen tube 441 does not disturb the operation of %he endoscope, and this improves the operability of the endoscope.

As the conduit tube which passes through the port portion and extends rearward, a plurality of tubes combined as one tube may be employed in place of the aforementioned multi-lumen tube.

Figure 34:
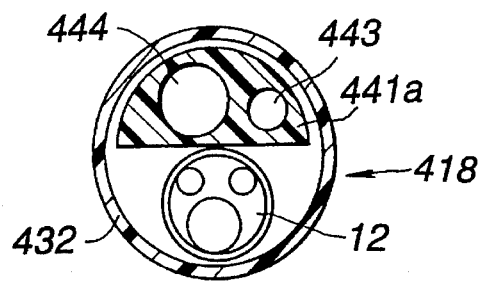
FIG. 34 is a lateral cross-sectional view showing a first example of a conduit tube provided in the endoscope cover.
Figure 35:
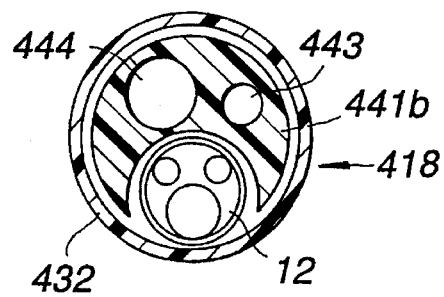
FIG. 35 is a lateral cross-sectional view showing a second example of a conduit tube provided in the endoscope cover.
Figure 36:
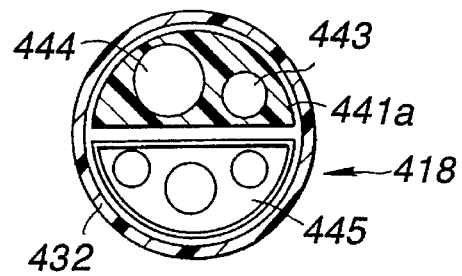
FIG. 36 is a lateral cross-sectional view showing a third example of a conduit tube provided in the endoscope cover.

Examples of the structure of the conduit tube provided in the endoscope cover are shown in FIGS. 34 through 36.

FIG. 34 is a cross-sectional view showing a first example. A multi-lumen tube 441a provided in the inserted portion covering portion 418 and having a gas/liquid channel 443 and a treatment tool channel 444 has a semi-circular cross-section.

FIG. 35 is a cross-sectional view showing a second example. A multi-lumen tube 441b provided in the inserted portion covering portion 418 and having a gas/liquid channel 443 and a treatment tool channel 444 has a crescent-like cross-sectional form which surrounds the inserted portion 12 of the covered endoscope.

FIG. 36 is a cross-sectional view showing a third example which is a modification of the first example. In this example, a multi-lumen tube 441a having a semi-circular cross-section is provided, and an inserted portion 445 of the endoscope also has a semi-circular cross-sectional form.

When the conduit tube is a multi-lumen tube having a cross-sectional form other than the circular cross-section, the movement of the contents of the endoscope cover, such as the multi-lumen tube, which would otherwise be generated when the inserted portion of the covered type endoscope is curved, can be restricted. Furthermore, in the second example in which the inserted portion of the endoscope is surrounded by the multi-lumen tube or in the third embodiment in which both the multi-lumen tube and the inserted portion of the endoscope have a semi-circular cross-sectional form, the movement of the contents of the endoscope cover can further be restricted.

Figure 37:
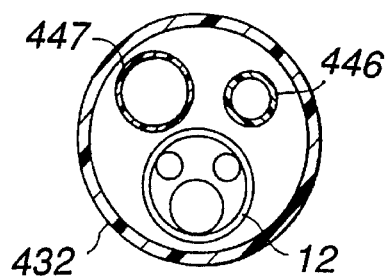
FIG. 37 is a lateral cross-sectional view of a conventional standard conduit tube provided in the endoscope cover.
Figure 38:
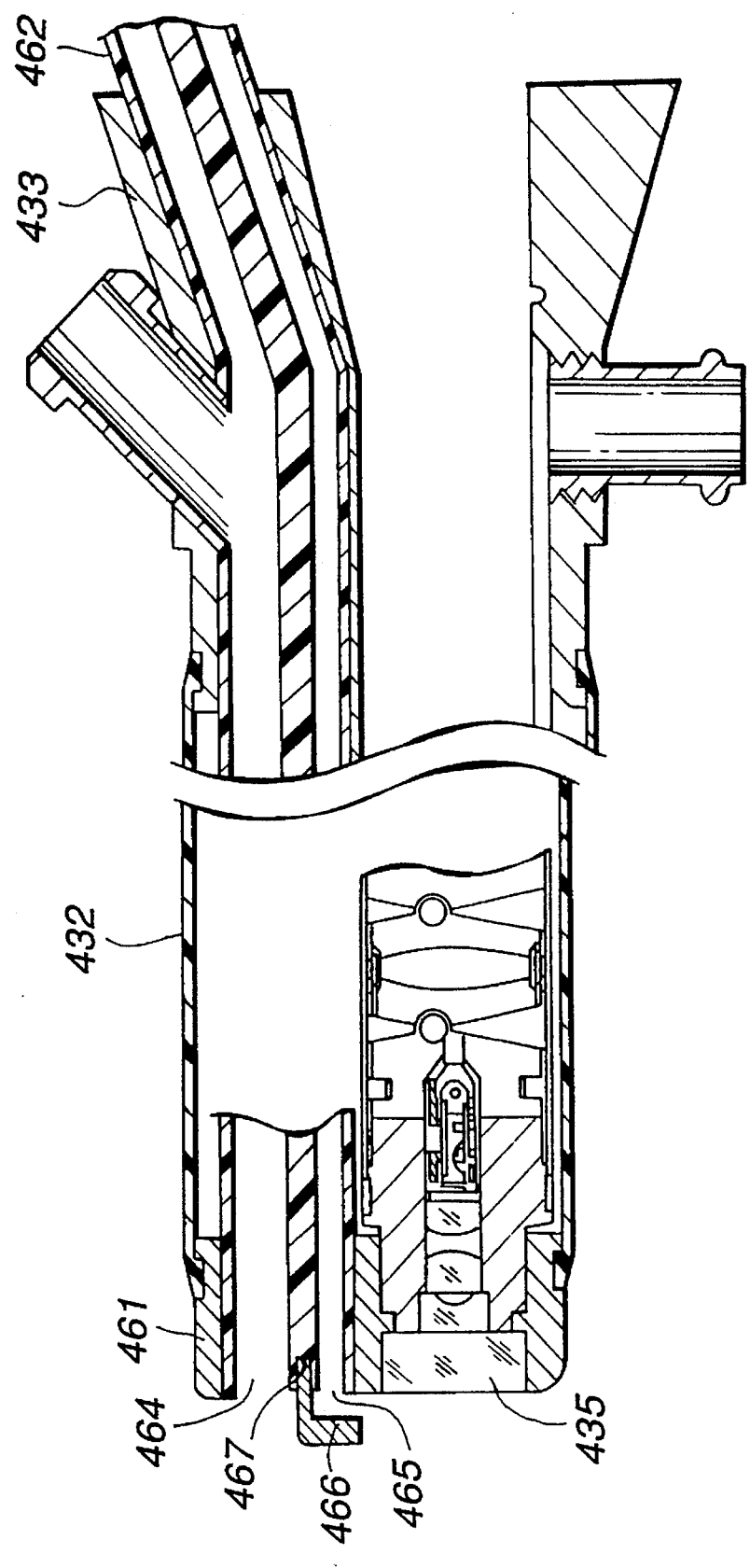
FIG. 38 is a cross-sectional view of an endoscope cover showing a first modification of the distal end constituting portion of the ninth embodiment endoscope cover according to the present invention.

Generally, the conduit tube provided in the endoscope cover is constituted by a plurality of independent circular tubes, such as a gas/liquid tube 446 and a treatment tool channel tube 447, as shown in FIG. 37. In that case, the contents of the endoscope cover, such as the conduit tube, may move during the curving operation or the like, adversely affecting the inserting property of the treatment tool or the durability of the cover. However, since the conduit tube is constituted by a multi-lumen tube having a cross-sectional form other than the circular cross-section in this embodiment, the movement of the contents of the endoscope cover can be restricted, while the inserting property of the treatment tool or the durability of the cover can be improved.

Modifications of the gas/liquid nozzle provided in the distal end constituting portion of the endoscope cover shown in the ninth embodiment will be described below.

FIGS. 38 through 41 show a first modification of the distal end constituting portion of the endoscope cover.

Figure 39:
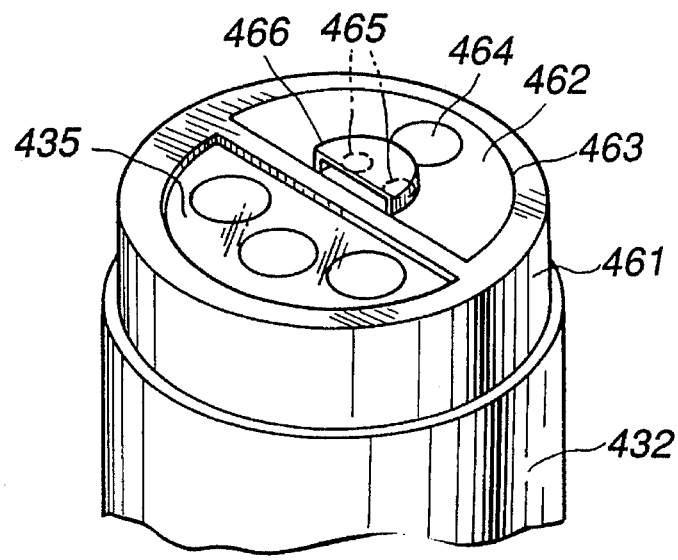
FIG. 39 is a perspective view of the cover distal end constituting portion of FIG. 38.
Figure 41:
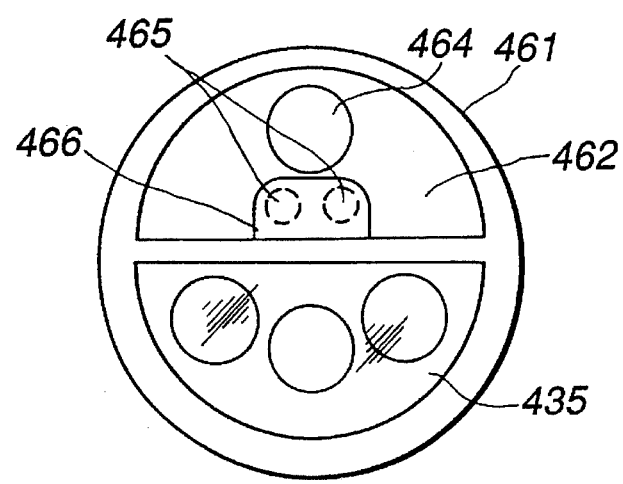
FIG. 41 is a front view of the cover distal end constituting portion of FIG. 38.

In the first modification, a multi-lumen tube 462 inserted into the endoscope cover and having a gas/liquid channel and a treatment tool channel passes through a cover distal end constituting portion 461. The end surface of the multi-lumen tube 462 extends to the distal end surface of the distal end constituting portion 461. In the distal end constituting portion 461, a semi-circular tube fitting hole 463 whose cross-sectional form matches the cross-sectional form of the multi-lumen tube 462 is provided in such a manner that in opens to the distal end surface, as shown in FIG. 39, and the multi-lumen tube 462 is fitted into and fixed to this tube fitting hole 463 in a state wherein the distal end surface of the tube is exposed. FIG. 41 is a view of the cover distal end constituting portion of FIG. 39 as seen when looking from the distal end side thereof.

A treatment tool channel and gas/liquid channels in the multi-lumen tube 462 are open at a treatment tool channel open portion 464 and gas/liquid channel open portions 465 formed at the distal end portion thereof, respectively. A lid member 466 which is open at the side thereof is mounted on the gas/liquid channel open portions 465 in such a manner that it surrounds the open portion 465. The lid member 466 has the function of a gas/liquid nozzle which directs the opening of the gas/liquid channels toward the cover glass 435.

Figure 40:
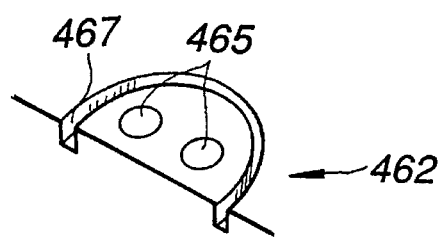
FIG. 40 is a perspective view of a gas/liquid nozzle fitting portion in the distal end constituting portion of FIG. 38.

As shown in FIG. 40, a semi-circular groove portion 467 is formed in the distal end surface of the multi-lumen tube 462 around the gas/liquid channel open portion 465. The lid member 466 is fitted and adhered to the groove portion 467 so that the lid member 466 covers the front and periphery of each of the gas/liquid channel open portions 465 and thereby make the gas/liquid channels open toward the cover glass 435.

Since the cover distal end constituting portion is constructed such that the conduit tube extends to the distal end surface thereof, the channel distal end portion can be constructed only by forming a hole in the distal end constituting portion through which the conduit tube passes, and the structure of the distal end constituting portion can thus be simplified That is the need for forming a nozzle, forming a conduit which communicates with the nozzle and providing a connection pipe for the channel tube is eliminated, and works whose part unit price and assembly cost are high can thus be omitted. It is therefore possible to provide an inexpensive endoscope cover.

Figure 42:
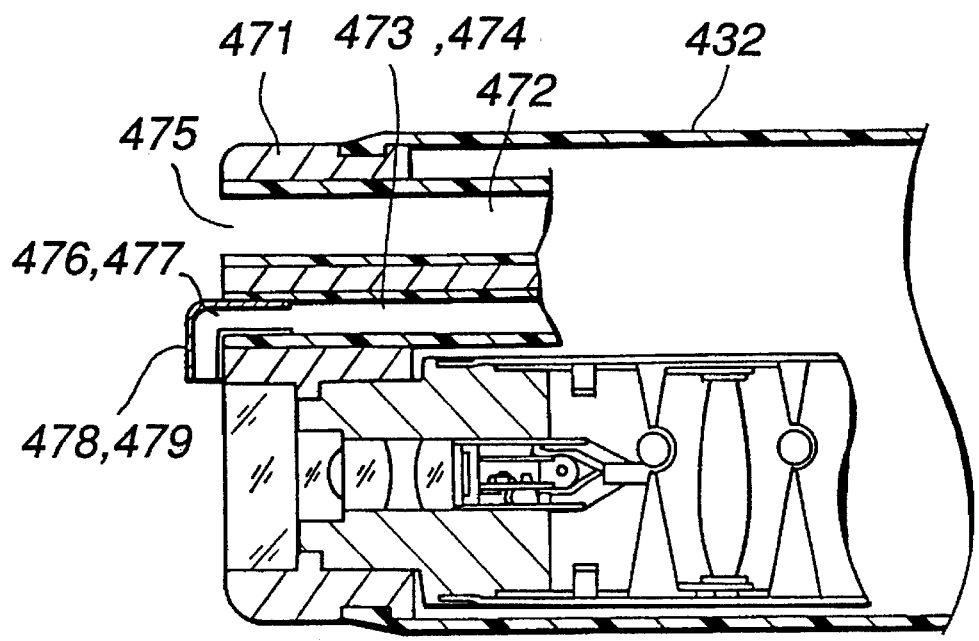
FIG. 42 is a cross-sectional view showing a second modification of the distal end constituting portion of the ninth embodiment of the endoscope cover according to the present invention.
Figure 43:
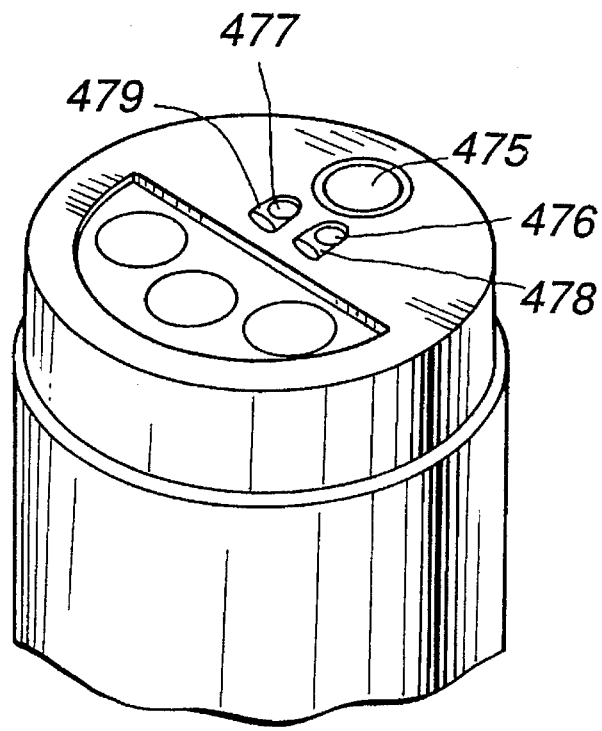
FIG. 43 is a perspective view of the cover distal end constituting portion of FIG. 42.
Figure 44:
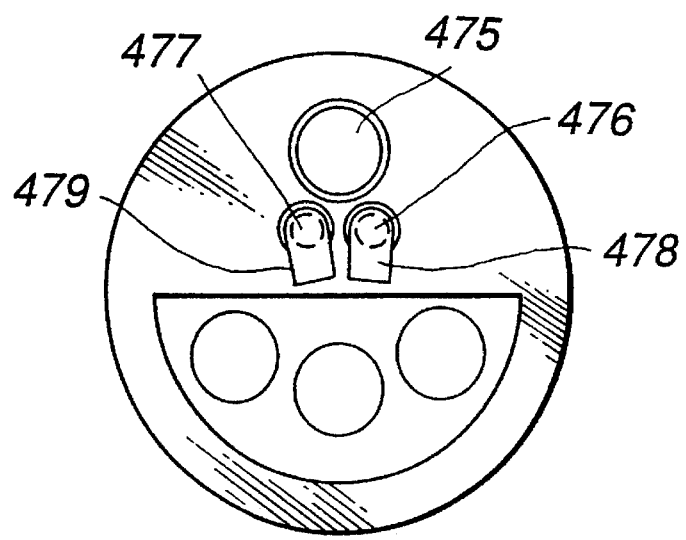
FIG. 44 is a front view of the distal end constituting portion of FIG. 42.

FIGS. 42 through 44 show a second modification of the distal end constituting portion of the endoscope cover.

In the second modification, a plurality of independent conduit tubes pass through a cover distal end constituting portion 471 in such a manner that the end surface of each of the conduit tubes reaches the distal end surface of the distal end constituting portion 471. More specifically, a treatment tool channel tube 472, a gas tube 473 and a liquid tube 474 are provided in the endoscope cover, and the respective tubes are fitted into and adhered to tube fitting holes in such a manner that the distal end surface of each of the tubes is exposed.

As shown in FIGS. 42 through 44, the treatment tool channel tube 472, the gas tube 473 and the liquid tube 474 are open at a treatment tool channel open portion 475, a gas channel open portion 476 and a liquid channel open portion 477 formed in %he distal end portion thereof, respectively. A gas nozzle 478 and a liquid nozzle 479 are respectively fitted into and adhered to the gas channel open portion 476 and the liquid channel open portion 477.

Thus, even where the conduit tubes are provided separately to form the channels, since the cover distal end constituting portion is constructed such that the conduit tubes extend to the distal end surface thereof, the structure of the distal end constituting portion can be simplified, as in the case of the first modification, and an inexpensive endoscope cover can thus be provided.

The present invention may be embodied in several forms without departing from the spirit of essential characteristics thereof. The scope of the invention is defined by the appended claims rather than by the description of the embodiments.

What is claimed is:

1. An improved endoscope cover with a channel, said improved endoscope cover having a treatment tool channel into which a treatment tool is inserted, said improved endoscope cover being detachable from and covering at least an inserted portion of an endoscope, the improvement comprising:

said treatment tool channel being connected to said endoscope cover in such a manner that a rear end portion of said treatment tool channel is slidable relative to an endoscope operating portion fixing port portion provided in a rear end portion of said improved endoscope cover.

2. An improved endoscope cover with a channel, said improved endoscope cover having a treatment tool channel into which a treatment tool is inserted, said improved endoscope cover being detachable from and covering at least an inserted portion of an endoscope, the improvement comprising:

said treatment tool channel being connected to said endoscope cover in such a manner that a rear end portion of said treatment tool channel is slidable relative to an endoscope operating portion fixing port portion provided in a rear end portion of said endoscope cover, and wherein a movement restriction means for restricting an amount of movement of said treatment tool channel at least in either of rotational and longitudinal directions of said channel is provided in said endoscope operating portion fixing port portion.

* * * * *